(12) United States Patent
Tallarida et al.

(10) Patent No.: US 11,154,687 B2
(45) Date of Patent: Oct. 26, 2021

(54) CATHETER PATENCY SYSTEMS AND METHODS

(71) Applicant: Versago Vascular Access, Inc., West Bridgewater, MA (US)

(72) Inventors: Steven J. Tallarida, Mansfield, MA (US); John M. Butziger, East Greenwich, RI (US); Richard P. Rodgers, Hudson, MA (US)

(73) Assignee: VERSAGO VASCULAR ACCESS, INC., West Bridgewater, MA (US)

( * ) Notice: Subject to any disclaimer, the term of this patent is extended or adjusted under 35 U.S.C. 154(b) by 0 days.

(21) Appl. No.: 14/974,851

(22) Filed: Dec. 18, 2015

(65) Prior Publication Data

US 2016/0175560 A1 Jun. 23, 2016

Related U.S. Application Data

(60) Provisional application No. 62/093,750, filed on Dec. 18, 2014.

(51) Int. Cl.
*A61M 25/00* (2006.01)
*A61M 39/02* (2006.01)
*A61M 5/142* (2006.01)

(52) U.S. Cl.
CPC .... *A61M 25/0017* (2013.01); *A61M 39/0247* (2013.01); *A61M 2005/14284* (2013.01); *A61M 2025/0018* (2013.01); *A61M 2025/0019* (2013.01); *A61M 2039/0258* (2013.01); *A61M 2039/0261* (2013.01); *A61M 2039/0273* (2013.01); *A61M 2039/0282* (2013.01)

(58) Field of Classification Search
CPC ...... A61M 2025/0019; A61M 25/0017; A61M 39/0247
See application file for complete search history.

(56) References Cited

U.S. PATENT DOCUMENTS

| | | |
|---|---|---|
| 975,285 A | 11/1910 | Lymburner |
| 3,757,585 A | 9/1973 | Heller et al. |
| 3,819,282 A | 6/1974 | Schultz |
| 4,096,896 A | 6/1978 | Engel |
| 4,181,132 A | 1/1980 | Parks |
| 4,190,040 A | 2/1980 | Schulte |

(Continued)

FOREIGN PATENT DOCUMENTS

| | | |
|---|---|---|
| AU | 2016294584 | 1/2018 |
| AU | 2015364382 | 7/2020 |

(Continued)

OTHER PUBLICATIONS

U.S. Office Action dated Dec. 2, 2014, issued in U.S. Appl. No. 13/770,732, 15 pages.

(Continued)

*Primary Examiner* — Spencer E. Bell
(74) *Attorney, Agent, or Firm* — Grossman, Tucker, Perreault & Pfleger, PLLC

(57) ABSTRACT

A patency system for maintaining a patency of an indwelling medical device including an elongated shaft configured to be at least partially received within a portion of the indwelling medical device, and at least one cleaner configured to at least partially dislodge debris formed within the indwelling medical device.

21 Claims, 24 Drawing Sheets

(56) References Cited

U.S. PATENT DOCUMENTS

| | | |
|---|---|---|
| 4,228,802 A | 10/1980 | Trott |
| 4,445,896 A | 5/1984 | Gianturco |
| 4,543,088 A | 9/1985 | Boatman et al. |
| 4,576,595 A | 3/1986 | Aas et al. |
| 4,673,394 A | 6/1987 | Fenton, Jr. et al. |
| 4,676,782 A | 6/1987 | Yamamoto et al. |
| 4,692,146 A | 9/1987 | Hilger |
| 4,710,167 A | 12/1987 | Lazorthes |
| 4,760,837 A | 8/1988 | Petit |
| 4,760,844 A | 8/1988 | Kyle |
| 4,781,680 A | 11/1988 | Redmond et al. |
| 4,802,885 A | 2/1989 | Weeks et al. |
| 4,840,615 A | 6/1989 | Hancock et al. |
| 4,892,518 A | 1/1990 | Cupp et al. |
| 4,904,241 A | 2/1990 | Bark |
| 4,919,653 A | 4/1990 | Martinez et al. |
| 4,929,236 A | 5/1990 | Sampson |
| 5,003,657 A | 4/1991 | Boiteau et al. |
| 5,006,115 A | 4/1991 | McDonald |
| 5,013,316 A | 5/1991 | Goble et al. |
| 5,041,098 A | 8/1991 | Loiterman et al. |
| 5,057,084 A | 10/1991 | Ensminger et al. |
| 5,084,015 A | 1/1992 | Moriuchi |
| 5,120,221 A | 6/1992 | Orenstein et al. |
| 5,137,529 A | 8/1992 | Watson et al. |
| 5,180,365 A | 1/1993 | Ensminger et al. |
| 5,203,771 A | 4/1993 | Melker et al. |
| 5,213,574 A | 5/1993 | Tucker |
| 5,215,530 A | 6/1993 | Hogan |
| 5,217,462 A | 6/1993 | Asnis et al. |
| 5,234,406 A | 8/1993 | Dransner et al. |
| 5,281,199 A | 1/1994 | Ensminger et al. |
| 5,295,658 A | 3/1994 | Atkinson et al. |
| 5,306,255 A | 4/1994 | Haindl |
| 5,318,545 A | 6/1994 | Tucker |
| 5,332,398 A | 7/1994 | Miller et al. |
| 5,337,756 A | 8/1994 | Barbier et al. |
| 5,350,360 A * | 9/1994 | Ensminger ........ A61M 39/0606 604/288.03 |
| 5,352,204 A | 10/1994 | Ensminger |
| 5,360,407 A | 11/1994 | Leonard |
| 5,387,192 A | 2/1995 | Glantz et al. |
| 5,391,801 A | 2/1995 | Sato et al. |
| 5,399,168 A | 3/1995 | Wadsworth, Jr. et al. |
| 5,417,656 A | 5/1995 | Ensminger et al. |
| 5,423,334 A | 6/1995 | Jordan |
| 5,476,460 A | 12/1995 | Montalvo |
| 5,498,265 A | 3/1996 | Asnis et al. |
| 5,520,643 A | 5/1996 | Ensminger et al. |
| 5,522,817 A | 6/1996 | Sander et al. |
| 5,527,278 A | 6/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,613,945 A | 3/1997 | Cai et al. |
| 5,637,088 A | 6/1997 | Wenner et al. |
| 5,643,267 A | 7/1997 | Hitomi et al. |
| 5,647,855 A | 7/1997 | Trooskin |
| 5,695,490 A | 12/1997 | Flaherty et al. |
| 5,702,413 A | 12/1997 | Lafontaine |
| 5,704,915 A | 1/1998 | Melsky et al. |
| 5,718,682 A | 2/1998 | Tucker |
| 5,718,692 A | 2/1998 | Schon et al. |
| 5,792,104 A | 8/1998 | Speckman et al. |
| 5,792,123 A | 8/1998 | Ensminger |
| 5,797,879 A | 8/1998 | DeCampli |
| 5,833,654 A | 11/1998 | Powers et al. |
| 5,836,935 A | 11/1998 | Ashton et al. |
| 5,843,069 A | 12/1998 | Butler et al. |
| 5,848,989 A | 12/1998 | Villani |
| 5,928,236 A | 7/1999 | Augagneur et al. |
| 5,931,801 A | 8/1999 | Burbank et al. |
| 5,951,512 A | 9/1999 | Dalton |
| 5,954,691 A | 9/1999 | Prosl |
| 5,989,206 A | 11/1999 | Prosl et al. |
| 6,007,516 A | 12/1999 | Burbank et al. |
| 6,030,397 A | 2/2000 | Monetti et al. |
| 6,039,712 A | 3/2000 | Fogarty et al. |
| 6,045,573 A | 4/2000 | Wenstrom, Jr. et al. |
| 6,048,343 A | 4/2000 | Mathis et al. |
| 6,056,751 A | 5/2000 | Fenton, Jr. |
| 6,113,572 A | 9/2000 | Gailey et al. |
| 6,139,565 A | 10/2000 | Stone et al. |
| 6,190,352 B1 | 2/2001 | Haarala et al. |
| 6,213,973 B1 | 4/2001 | Eliasen et al. |
| 6,413,260 B1 | 7/2002 | Berrevoets et al. |
| 6,478,783 B1 | 11/2002 | Moorehead |
| 6,527,754 B1 | 3/2003 | Tallarida et al. |
| 6,607,504 B2 | 8/2003 | Haarala et al. |
| 6,655,240 B1 | 12/2003 | DeVecchis et al. |
| 6,699,331 B1 | 3/2004 | Kritzler |
| 6,962,577 B2 | 11/2005 | Tallarida et al. |
| 6,981,977 B2 | 1/2006 | Herweck et al. |
| 7,056,316 B1 | 6/2006 | Burbank et al. |
| 7,131,962 B1 | 11/2006 | Estabrook et al. |
| 7,172,574 B2 | 2/2007 | Lundgren et al. |
| 7,272,997 B1 | 9/2007 | Lee et al. |
| 7,351,233 B2 | 4/2008 | Parks |
| 7,452,354 B2 | 11/2008 | Bright et al. |
| 7,618,462 B2 | 11/2009 | Ek |
| 7,713,251 B2 | 5/2010 | Tallarida et al. |
| 7,727,235 B2 | 6/2010 | Contiliano et al. |
| 7,803,143 B2 | 9/2010 | Tallarida et al. |
| 7,811,266 B2 | 10/2010 | Eliasen |
| 7,824,365 B2 | 11/2010 | Haarala et al. |
| 7,959,615 B2 | 6/2011 | Stats et al. |
| 8,182,453 B2 | 5/2012 | Eliasen |
| 8,377,034 B2 | 2/2013 | Tallarida et al. |
| 8,409,153 B2 | 4/2013 | Tallarida et al. |
| 8,529,525 B2 | 9/2013 | Gerber et al. |
| 8,641,676 B2 | 2/2014 | Butts et al. |
| 8,656,929 B2 | 2/2014 | Miller et al. |
| 8,721,620 B2 | 5/2014 | Imran |
| 9,060,809 B2 | 6/2015 | Tipirneni et al. |
| 9,295,773 B2 | 3/2016 | Prosl et al. |
| 9,480,831 B2 | 11/2016 | Tallarida et al. |
| 9,597,783 B2 | 3/2017 | Zhang |
| 9,764,124 B2 | 9/2017 | Tallarida et al. |
| 10,238,851 B2 | 3/2019 | Butziger et al. |
| 10,300,262 B2 | 5/2019 | Tallarida et al. |
| 10,369,345 B2 | 8/2019 | Tallarida et al. |
| 10,512,734 B2 | 12/2019 | Tallarida et al. |
| 10,835,728 B2 | 11/2020 | Tallarida et al. |
| 10,905,866 B2 | 2/2021 | Tallarida et al. |
| 2001/0016713 A1 | 8/2001 | Takagi et al. |
| 2001/0037094 A1 | 11/2001 | Adaniya et al. |
| 2002/0095122 A1 | 7/2002 | Shaffer |
| 2002/0198527 A1 | 12/2002 | Muckter |
| 2003/0109837 A1 | 6/2003 | McBride-Sakal |
| 2004/0092875 A1 | 5/2004 | Kochamba |
| 2004/0097830 A1 | 5/2004 | Cooke et al. |
| 2004/0097930 A1 | 5/2004 | Justis et al. |
| 2004/0097941 A1 | 5/2004 | Weiner et al. |
| 2004/0147929 A1 | 7/2004 | Biedermann et al. |
| 2004/0158207 A1 | 8/2004 | Hunn et al. |
| 2004/0181150 A1 | 9/2004 | Evans et al. |
| 2005/0014993 A1 | 1/2005 | Mische |
| 2005/0015048 A1 | 1/2005 | Chiu et al. |
| 2005/0085778 A1* | 4/2005 | Parks ................ A61M 39/0208 604/288.02 |
| 2005/0124980 A1 | 6/2005 | Sanders |
| 2005/0143735 A1 | 6/2005 | Kyle |
| 2005/0154373 A1 | 7/2005 | Deutsch |
| 2005/0165431 A1 | 7/2005 | Krivoruchko |
| 2005/0171493 A1* | 8/2005 | Nicholls ................ A61B 1/122 604/267 |
| 2005/0209619 A1 | 9/2005 | Johnson et al. |
| 2005/0267421 A1 | 12/2005 | Wing |
| 2006/0004325 A1 | 1/2006 | Hamatake et al. |
| 2006/0142705 A1 | 6/2006 | Halili |
| 2006/0178648 A1 | 8/2006 | Barron et al. |
| 2006/0224129 A1 | 10/2006 | Beasley et al. |

(56) References Cited

U.S. PATENT DOCUMENTS

| | | | |
|---|---|---|---|
| 2006/0264988 A1* | 11/2006 | Boyle | A61M 27/00 606/159 |
| 2006/0276749 A1 | 12/2006 | Selmon et al. | |
| 2007/0078432 A1 | 4/2007 | Halseth et al. | |
| 2007/0100302 A1 | 5/2007 | Dicarlo et al. | |
| 2007/0233019 A1 | 10/2007 | Forsell | |
| 2007/0265595 A1 | 11/2007 | Miyamoto et al. | |
| 2008/0039820 A1 | 2/2008 | Sommers et al. | |
| 2008/0114308 A1 | 5/2008 | di Palma et al. | |
| 2008/0243106 A1 | 10/2008 | Coe et al. | |
| 2008/0262475 A1 | 10/2008 | Preinitz | |
| 2010/0249491 A1 | 9/2010 | Farnan et al. | |
| 2011/0137288 A1 | 6/2011 | Tallarida et al. | |
| 2011/0152901 A1 | 6/2011 | Woodruff et al. | |
| 2011/0160699 A1 | 6/2011 | Imran | |
| 2011/0264058 A1 | 10/2011 | Linen et al. | |
| 2011/0282285 A1 | 11/2011 | Blanchard et al. | |
| 2011/0295206 A1 | 12/2011 | Gurley | |
| 2011/0301652 A1 | 12/2011 | Reed et al. | |
| 2011/0311602 A1* | 12/2011 | Mills | A01N 37/00 424/409 |
| 2012/0035585 A1 | 2/2012 | Kurrus et al. | |
| 2012/0053514 A1 | 3/2012 | Robinson et al. | |
| 2012/0136247 A1 | 5/2012 | Pillai | |
| 2012/0136366 A1 | 5/2012 | Pillai | |
| 2012/0209180 A1 | 8/2012 | Gray et al. | |
| 2012/0232501 A1 | 9/2012 | Eliasen | |
| 2013/0081728 A1 | 4/2013 | Alsaffar | |
| 2013/0116666 A1 | 5/2013 | Shih et al. | |
| 2013/0218103 A1 | 8/2013 | Tallarida et al. | |
| 2013/0226101 A1 | 8/2013 | Westcott | |
| 2013/0231637 A1 | 9/2013 | Tallarida et al. | |
| 2013/0274814 A1 | 10/2013 | Weiner et al. | |
| 2014/0102445 A1* | 4/2014 | Clement | A61M 25/00 128/202.13 |
| 2014/0142418 A1 | 5/2014 | Gurley et al. | |
| 2014/0188179 A1 | 7/2014 | McCormick | |
| 2014/0257165 A1 | 9/2014 | Shechtman et al. | |
| 2014/0277191 A1 | 9/2014 | Evans et al. | |
| 2015/0051584 A1 | 2/2015 | Korkuch et al. | |
| 2015/0182727 A1 | 7/2015 | Gurley et al. | |
| 2015/0273201 A1 | 10/2015 | Tallarida et al. | |
| 2016/0175560 A1 | 6/2016 | Tallarida et al. | |
| 2016/0175575 A1 | 6/2016 | Tallarida et al. | |
| 2016/0263352 A1 | 9/2016 | Gurley | |
| 2017/0000995 A1 | 1/2017 | Tallarida et al. | |
| 2017/0014611 A1 | 1/2017 | Butziger et al. | |
| 2017/0173273 A1 | 6/2017 | Tallarida et al. | |
| 2017/0246427 A1 | 8/2017 | Gurley | |
| 2017/0340814 A1 | 11/2017 | Miesel et al. | |
| 2018/0104465 A1 | 4/2018 | Tallarida et al. | |
| 2019/0192769 A1 | 6/2019 | Tallarida et al. | |
| 2019/0209808 A1 | 7/2019 | Gurley et al. | |
| 2019/0351209 A1 | 11/2019 | Butziger et al. | |
| 2020/0238021 A1 | 7/2020 | Tallarida et al. | |

FOREIGN PATENT DOCUMENTS

| | | |
|---|---|---|
| AU | 2015364276 | 8/2020 |
| EP | 1680174 | 7/2006 |
| EP | 2403431 | 1/2012 |
| EP | 3322460 | 5/2018 |
| EP | 3233175 | 3/2019 |
| EP | 3125970 | 5/2020 |
| GB | 2502291 | 11/2013 |
| JP | 55-065009 | 5/1980 |
| JP | 5506591 | 9/1993 |
| JP | 8500031 | 1/1996 |
| JP | 9-509852 | 10/1997 |
| JP | 2002119462 | 4/2002 |
| JP | 2002523131 | 7/2002 |
| JP | 2004167005 | 6/2004 |
| JP | 2004535234 | 11/2004 |
| JP | 2005522280 | 7/2005 |
| JP | 2008100084 | 5/2008 |
| JP | 2009-273598 | 11/2009 |
| JP | 2011120737 | 6/2011 |
| JP | 6837971 | 2/2021 |
| WO | 9701370 | 1/1997 |
| WO | 00/78231 | 12/2000 |
| WO | 0078231 | 12/2000 |
| WO | 2005025665 | 3/2005 |
| WO | 2005/094702 | 10/2005 |
| WO | 2007051563 | 5/2007 |
| WO | 2008126966 | 10/2008 |
| WO | 2009/148587 | 12/2009 |
| WO | 2011035387 | 3/2011 |
| WO | 2015153611 | 10/2015 |
| WO | 2015153976 | 10/2015 |
| WO | 2016/100868 | 6/2016 |
| WO | 2016/100945 | 6/2016 |
| WO | 2019126306 A1 | 6/2019 |

OTHER PUBLICATIONS

U.S. Office Action dated Jun. 10, 2015, issued in U.S. Appl. No. 13/770,732, 14 pages.
International Search Report and Written Opinion dated Jul. 2, 2015, issued in PCT Patent Application No. PCT/US2015/023590, 11 pages.
International Search Report and Written Opinion dated Jul. 10, 2015, issued in PCT Patent Application No. PCT/US2015/024256, 10 pages.
U.S. Office Action dated Aug. 10, 2015, issued in U.S. Appl. No. 14/231,392, 24 pages.
U.S. Office Action dated Jan. 15, 2016, issued in U.S. Appl. No. 13/770,732, 23 pages.
International Search Report and Written Opinion dated Feb. 26, 2016, issued in PCT Patent Application Serial No. PCT/US2015/066934, 11 pages.
International Search Report and Written Opinion dated Mar. 7, 2016, issued in PCT Patent Application Serial No. PCT/US2015/066778, 9 pages.
U.S. Office Action dated Nov. 30, 2016, issued in U.S. Appl. No. 14/231,392, 6 pages.
Final Office Action dated Mar. 22, 2016, issued in U.S. Appl. No. 14/231,392, 22 pages.
Notice of Allowance dated Jun. 15, 2016, issued in U.S. Appl. No. 13/770,732, 9 pages.
PCT International Search Report dated Nov. 21, 2001 issued in PCT Application No. PCT/US01/13749, 4 pages.
PCT Written Opinion dated Dec. 19, 2002 issued in PCT Application PCT/US01/13749, 5 pages.
PCT Preliminary Examination Report dated May 28, 2003 issued in PCT Application PCT/US01/13749, 2 pages.
European Examination Report dated Jul. 30, 2003 issued in European Patent Application No. 99 964 086.5, 5 pages.
U.S. Office Action dated Aug. 27, 2003 issued in U.S. Appl. No. 09/842,458, 8 pages.
U.S. Office Action dated Dec. 23, 2003 issued in U.S. Appl. No. 09/842,458, 7 pages.
European Examination Report dated Mar. 9, 2004 issued in European Patent Application No. 99 964 086.5, 4 pages.
U.S. Notice of Allowance dated Oct. 15, 2004 issued in U.S. Appl. No. 09/842,458, 7 pages.
Australian Examination Report dated Jan. 21, 2005 issued in Australian Patent Application No. 2001257388, 2 pages.
U.S. Notice of Allowance dated Feb. 24, 2005 issued in U.S. Appl. No. 09/842,458, 6 pages.
European Examination Report dated Mar. 1, 2005 issued in European Patent Application No. 99 964 086.5, 4 pages.
European Examination Report dated Mar. 30, 2005 issued in European Patent Application No. 99 964 086.5, 3 pages.
European Decision to Refuse dated Dec. 15, 2005 issued in European Patent Application No. 99 964 086.5, 9 pages.
U.S. Office Action dated Feb. 14, 2007 issued in U.S. Appl. No. 10/890,909, 12 pages.

(56) References Cited

OTHER PUBLICATIONS

U.S. Office Action dated Apr. 11, 2007 issued in U.S. Appl. No. 10/931,890, 7 pages.
U.S. Office Action dated Sep. 13, 2007 issued in U.S. Appl. No. 10/890,909, 11 pages.
U.S. Office Action dated Sep. 13, 2007 issued in U.S. Appl. No. 10/931,890, 7 pages.
Canadian Office Action dated Oct. 16, 2007 issued in Canadian Patent Application No. 2,407,643, 2 pages.
U.S. Office Action dated Feb. 21, 2008 issued in U.S. Appl. No. 11/269,098, 19 pages.
U.S. Office Action dated Jun. 9, 2008 issued in U.S. Appl. No. 10/931,890, 10 pages.
U.S. Office Action dated Oct. 30, 2008 issued in U.S. Appl. No. 11/269,098, 12 pages.
U.S. Office Action dated Dec. 23, 2008 issued in U.S. Appl. No. 10/931,890, 9 pages.
U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.
U.S. Office Action dated Aug. 3, 2009 issued in U.S. Appl. No. 10/931,890, 10 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Feb. 17, 2011 issued in U.S. Appl. No. 12/902,839, 17 pages.
U.S. Office Action dated Oct. 17, 2011 issued in U.S. Appl. No. 12/902,839, 11 pages.
Notice of Allowance dated Feb. 1, 2012 issued in U.S. Appl. No. 12/902,839, 7 pages.
European Office Action dated Oct. 23, 2012 issued in European Patent Application No. 01 930 898.0, 4 pages.
U.S. Office Action dated Feb. 28, 2007 issued in U.S. Appl. No. 10/374,000, 8 pages.
U.S. Office Action dated Aug. 28, 2007 issued in U.S. Appl. No. 10/374,000, 8 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated May 20, 2009 issued in U.S. Appl. No. 10/374,000, 10 pages.
Access technologies, The V-A-Pu . . . Vascular Access and Beyond, downloaded from internet Jul. 28, 2009, http://www.norfolkaccess.com/VAPs.html, 4 pages.
SyncMedical, Innovative Surgical Devices, Primo Port Products, downloaded from internet Jul. 28, 2009, http://www.syncmedical.com/primo-port, 2 pages.
Corrected Notice of Allowability dated Jul. 12, 2016, issued in U.S. Appl. No. 13/770,732, 6 pages.
Corrected Notice of Allowability dated Aug. 2, 2016, issued in U.S. Appl. No. 13/770,732, 6 pages.
International Search Report and Written Opinion dated Oct. 7, 2016, issued in PCT International Patent Application No. PCT/US2016/042272, 11 pages.
International Preliminary Report on Patentability dated Oct. 13, 2016, issued in PCT International Patent Application No. PCT/US2015/023590, 9 pages.
International Preliminary Report on Patentability dated Oct. 13, 2016, issued in PCT International Patent Application No. PCT/US2015/024256, 8 pages.
U.S. Office Action dated Oct. 23, 2014 issued in U.S. Appl. No. 13/477,997, 14 pages.
Search Report dated Nov. 8, 2017, issued in European Patent Application No. 15773029.2, 8 pages.
European Extended Search Report dated Nov. 27, 2017, issued in European Patent Application No. 15772648.0, 7 pages.
Office Action dated Nov. 30, 2017, issued in U.S. Appl. No. 15/210,268, 15 pages.
Preliminary Report on Patentability dated Jan. 25, 2018, issued in PCT Patent Application No. PCT/US2016/042272, 9 pages.
Office Action dated Jun. 27, 2018, issued in U.S. Appl. No. 15/300,625, 14 pages.
Extended Search Report dated Jul. 4, 2018, issued in European Patent Application No. 15871254.7, 5 pages.
Partial Supplementary Search Report dated Aug. 2, 2018, issued in European Patent Application No. 15871198.6, 13 pages.
Office Action dated Aug. 29, 2018, issued in U.S. Appl. No. 15/267,537, 8 pages.
Notice of Allowance dated Sep. 12, 2018, issued in U.S. Appl. No. 15/210,268, 12 pages.
Intent to Grant dated Oct. 4, 2018, issued in European Patent Application No. 15871254.7, 7 pages.
Office Action dated Mar. 27, 2018, issued in U.S. Appl. No. 14/975,638, 8 pages.
Office Action dated Nov. 30, 2018, issued in European Patent Application No. 15 772 648.0, 4 pages.
Office Action dated Dec. 25, 2018, issued in Japanese Patent Application No. 2017-503790, 12 pages. English language machine translation provided.
Examination Report dated Jan. 10, 2019, issued in Australian Patent Application No. 2015240953, 5 pages.
Office Action dated Feb. 6, 2019, issued in U.S. Appl. No. 15/301,498, 10 pages.
Office Action dated Oct. 17, 2018, issued in U.S. Appl. No. 15/301,498, 14 pages.
Notice of Allowance dated Oct. 30, 2018, issued in U.S. Appl. No. 15/210,268, 11 pages.
Office Action dated Dec. 10, 2018, issued in U.S. Appl. No. 14/975,638, 16 pages.
Notice of Allowance dated Jan. 10, 2019, issued in U.S. Appl. No. 15/267,537, 8 pages.
Extended Search Report dated Dec. 12, 2018, issued in European Patent Application No. 15871198.6, 15 pages.
Examination Report dated Jan. 16, 2019, issued in Australian Patent Application No. 2015240568, 5 pages.
Decision to Grant dated Feb. 5, 2019, issued in Japanese Patent Application No. 2017-503777, 4 pages.
Extended Search Report dated Mar. 1, 2019, issued in European Patent Application No. 16825172.6, 7 pages.
Notice of Allowance dated Mar. 18, 2019, issued in U.S. Appl. No. 15/300,625, 8 pages.
International Search Report and Written Opinion dated Mar. 21, 2019, issued in PCT International Patent Application No. PCT/US2018/066472, 9 pages.
Notice of Allowance dated Jul. 3, 2019, issued in Australian Patent Application No. 2015240953, 4 pages.
Notice of Allowance dated Aug. 8, 2019, issued in Australian Patent Application No. 2015240568, 4 pages.
Examination Report dated Aug. 14, 2019, issued in Australian Patent Application No. 2015364276, 4 pages.
Examination Report dated Aug. 21, 2019, issued in Australian Patent Application No. 2015364382, 5 pages.
Notice of Allowance dated Aug. 27, 2019, issued in U.S. Appl. No. 15/301,498, 10 pages.
Office Action dated Sep. 18, 2019, issued in U.S. Appl. No. 14/975,638, 15 pages.
Office Action dated Oct. 1, 2019, issued in Japanese Patent Application No. 2017-532627, 9 pages.
Office Action dated Oct. 1, 2019, issued in Japanese Patent Application No. 2017-532615, 5 pages.
Office Action dated Nov. 26, 2019, issued in U.S. Appl. No. 15/835,858, 15 pages.
Intent to Grant dated Dec. 10, 2019, issued in European Patent Application No. 15 773 029.2, 6 pages.
Office Action dated Mar. 27, 2020, issued in U.S. Appl. No. 14/975,638, 12 pages.
Notice of Allowance dated May 12, 2020, issued in U.S. Appl. No. 15/835,858, 9 pages.

(56) References Cited

OTHER PUBLICATIONS

Office Action dated Jun. 18, 2020, issued in Japanese Patent Application No. 2017-565905, 11 pages.
Examination Report dated May 20, 2020, issued in European Patent Application No. 15 772 648.0, 4 pages.
Office Action dated Jun. 2, 2020, issued in Japanese Patent Application No. 2017-532627, 6 pages.
Decision to Grant dated Feb. 4, 2020, issued in Japanese Patent Application No. 2017-532615, 4 pages. English language summary provided.
Examination Report dated Mar. 23, 2020, issued in Australian Patent Application No. 2016294584, 6 pages.
Notice of Acceptance dated Apr. 20, 2020, issued in Australian Patent Application No. 2015364276, 4 pages.
Notice of Allowance dated Oct. 1, 2020, issued in U.S. Appl. No. 14/975,638, 12 pages.
Office Action dated Dec. 7, 2020, issued in U.S. Appl. No. 16/364,555, 24 pages.
Notice of Allowance dated Mar. 17, 2021, issued in U.S. Appl. No. 16/225,598, 8 pages.
Decision to Grant dated Apr. 1, 2021, issued in Japanese Patent Application No. 2017-565905, 6 pages.
Intent to Grant dated Apr. 12, 2021, issued in European Patent Application No. 15772648.0, 7 pages.
Office Action dated Apr. 16, 2021, issued in Canadian Patent Application No. 2,944,434, 5 pages.

\* cited by examiner

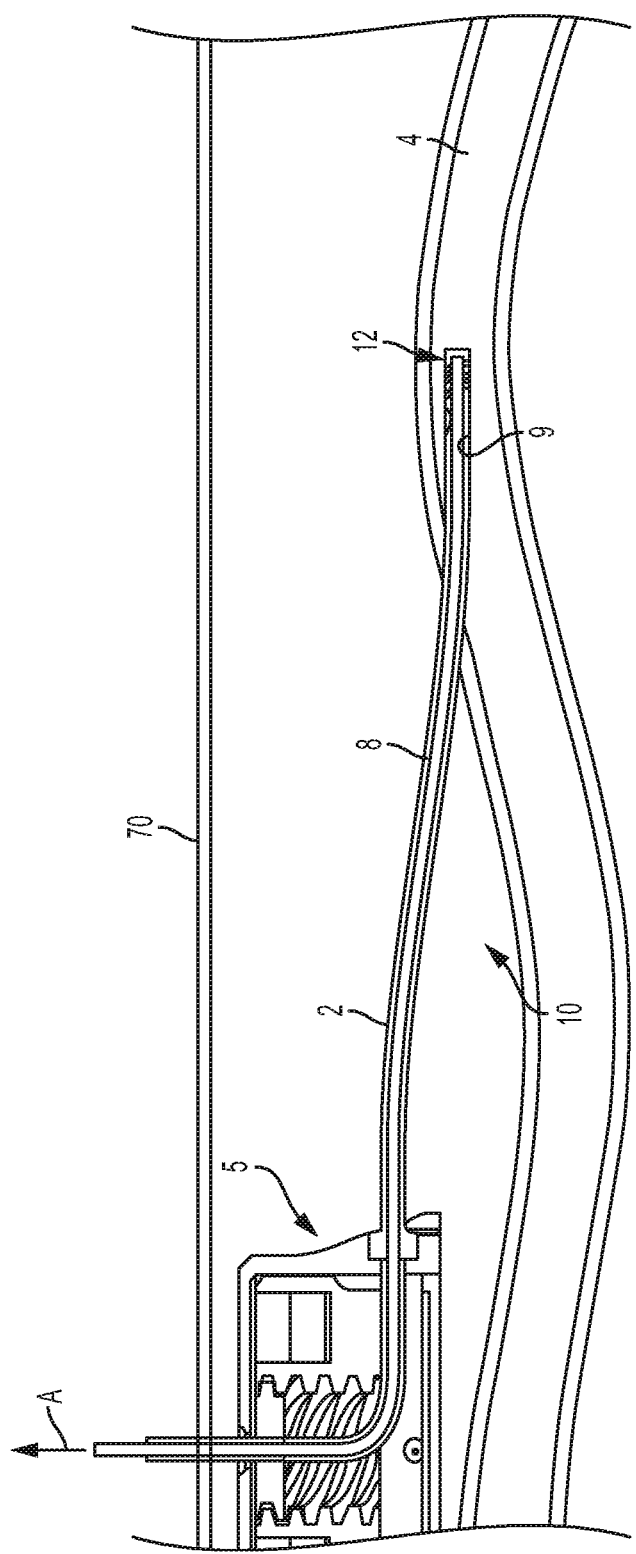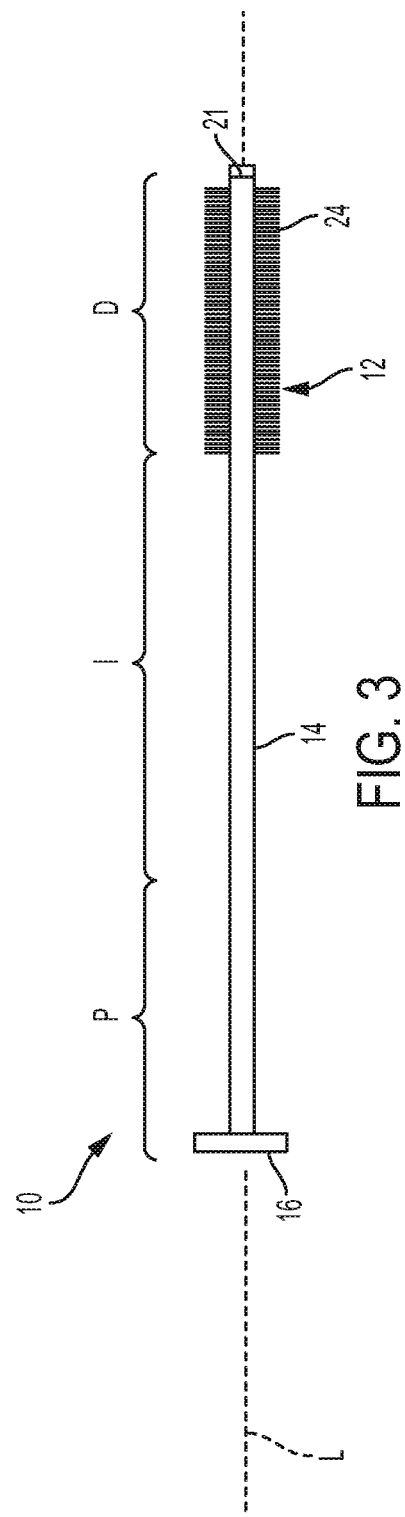

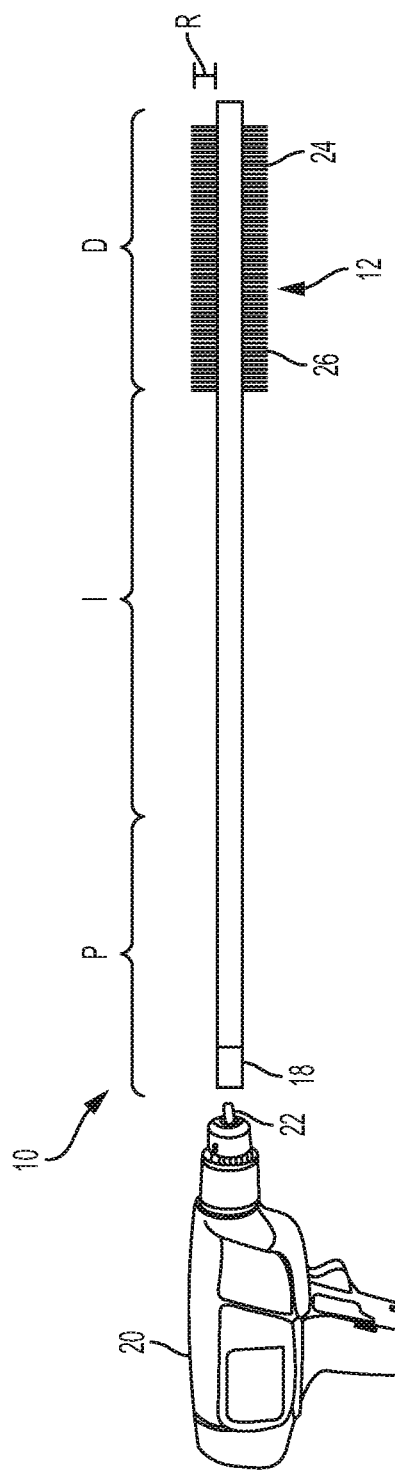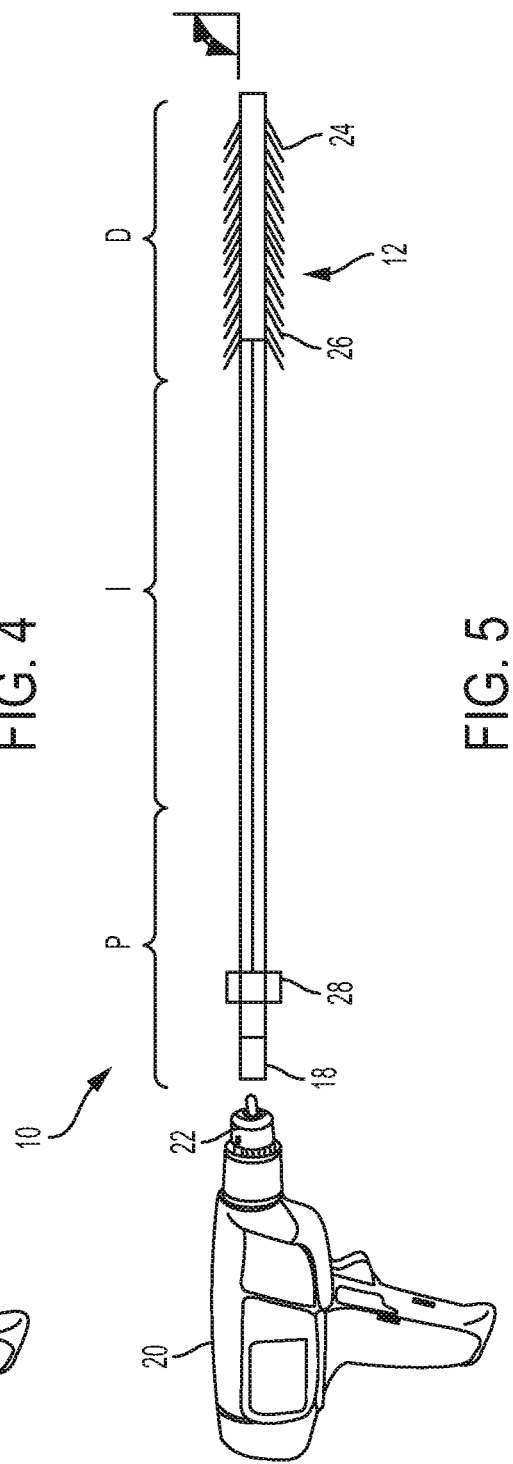
FIG. 4
FIG. 5

CATHETER PATENCY SYSTEMS AND METHODS

CROSS-REFERENCE TO RELATED APPLICATIONS

The present application claims the benefit of the filing date of U.S. provisional patent application Ser. No. 62/093,750 filed Dec. 18, 2014, the entire disclosure of which is incorporated herein by reference.

FIELD

The present disclosure relates to systems, devices and methods for maintaining catheter patency, and more particularly, systems, devices and method for maintaining patency of indwelling vascular access catheters.

BACKGROUND

Indwelling catheters are used, either alone or in combination with implantable medical devices (such as, but not limited to, implantable access ports) to provide access to the vasculature of a host for delivery of materials (e.g., drugs) and/or for removal/replacement of materials (e.g., blood). Over time, in-growth and clotting may clog indwelling catheters, either reducing fluid flow or completely preventing fluid flow through the catheter.

One method of trying to maintain patency of the catheter includes flushing the catheter with saline or other fluid agents, but these approaches may have only limited success. Once in-growth has begun, the efficacy of flushing alone may become limited, and clogging may ensue. Moreover, material removed from the catheter by the flushing may deposited into the vasculature of the host, particularly elsewhere in the circulatory system.

FIGURES

Features and advantages of the claimed subject matter will be apparent from the following detailed description of some example embodiments consistent therewith, which description should be considered with reference to the accompanying drawings, wherein:

FIG. 2 is a cross-sectional view of an embodiment of a catheter patency system disposed within the indwelling catheter system of FIG. 1;

FIG. 3 is a cross-sectional view of an embodiment of a catheter patency system consistent with the present disclosure;

FIG. 4 is a cross-sectional view of another embodiment of a catheter patency system in an extended position consistent with the present disclosure;

FIG. 5 is a cross-sectional view of the catheter patency system of FIG. 4 in a retracted position consistent with the present disclosure;

DETAILED DESCRIPTION

Figure 1:
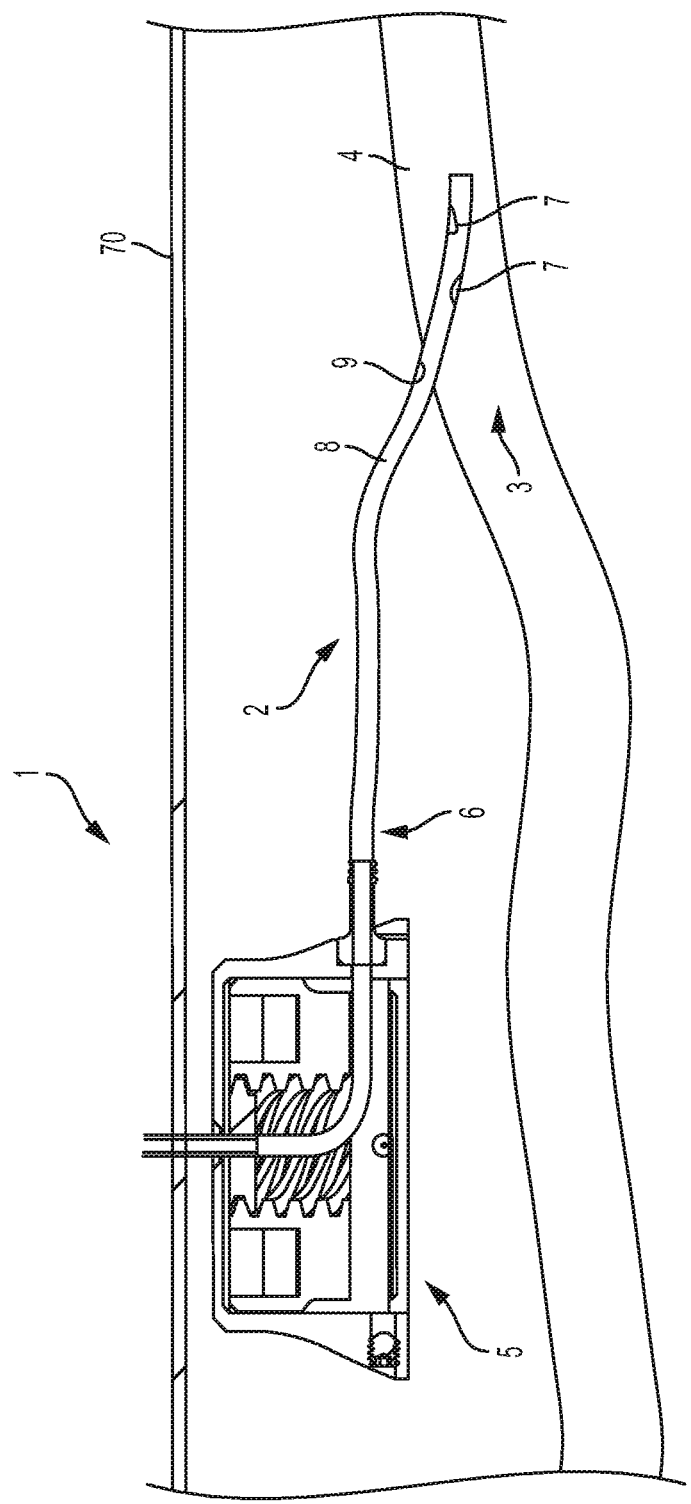
FIG. 1 is a cross-sectional view of an indwelling medical system, and more particularly an indwelling catheter system, consistent with the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this disclosure as suitable. In other words, features between the various exemplary embodiments described herein are interchangeable as suitable, and not exclusive.

By way of a general overview, the present disclosure may feature systems, devices, and/or methods for maintaining patency of an indwelling medical system. The systems, devices, and/or methods according to at least one embodiment of the present disclosure include a patency system having an elongated shaft and one or more cleaners configured to be at least partially disposed within the indwelling medical system. The cleaners are configured to dislodge debris (e.g. in-growth) forming within the indwelling medical system (e.g., a lumen of an indwelling catheter and/or a vascular access port), and may include one or more cleaners, such as one or more brushes, augers, jets, protrusions and strands. The patency system may optionally include one or more balloons, movable seals and/or valves configured to seal against a portion of the indwelling medical system, such as the indwelling catheter, to prevent dislodged debris from entering into the host's circulatory system or elsewhere in the indwelling catheter. The patency system may also optionally include one or more flushing sources and/or vacuum sources to facilitate the removal of dislodged debris from the indwelling medical system.

The patency system according to the present disclosure may be used to maintain the patency of an indwelling medical system. Referring now to FIG. 1, one embodiment of an indwelling medical system 1 according to the present disclosure is generally illustrated, which may comprise one or more medical devices. The indwelling medical system 1 may include a first medical device in the form of an implantable (indwelling) vascular access catheter 2 having a first end 3 configured to be inserted into a lumen 4 of a blood vessel in the tissue of a host (e.g. patient) for which a fluid is to be delivered (e.g. blood, medication) and/or withdrawn (e.g. blood).

Optionally, the indwelling medical system 1 may include a second medical device, such as in the form of a vascular access port 5 coupled to a second end 6 of the indwelling vascular access catheter 2.

Examples of the indwelling medical systems, and tools for use therewith, may include, but are not limited to, those described in U.S. patent application Ser. No. 10/890,909, filed Jul. 13, 2004; U.S. patent application Ser. No. 11/234,497, filed Oct. 4, 2005; U.S. patent application Ser. No. 14/231,392, filed Mar. 31, 2014; U.S. Patent Application Ser. No. 61/974,807, filed Apr. 3, 2014; U.S. Pat. Nos. 5,906,596; 6,527,754; 7,803,143; 7,803,143; 7,811,266; and 8,377,034, all of which are incorporated herein by reference, to the extent they are consistent with the present disclosure.

While the indwelling medical system 1 illustrated in FIG. 1 is shown to have a single indwelling catheter 2 with a single lumen 8, it should be appreciated that the indwelling catheter 2 may have a plurality of lumens 8, or the indwelling medical system 1 may include a plurality of indwelling catheters 2, with each catheter 2 having one or more lumens 8. Also, the indwelling catheter 2 may form an integral (e.g., unitary or one-piece) component with the vascular access port 5.

For ease of explanation, the patency system will be described in combination with an indwelling medical system 1 having an indwelling catheter 2. As such, the patency system may be referred to as a catheter patency system and the indwelling medical system may be referred to as an indwelling catheter system. It should be appreciated, however, that the patency system according to the present disclosure may be used to maintain the patency of any indwelling medical system and/or medical device with or without a catheter.

As can be seen, in-growth, hereinafter referred to as debris 7, which may include clotting such as fibrin and coagulum, may form within a portion of the indwelling medical system 1 such as, but not limited to, lumen 8. More particularly, the debris 7 may form on the interior surface 9 of the lumen 8 anywhere along the length thereof (i.e. the vascular access port 5 and/or the indwelling catheter 2). The debris 7, if left untreated, may reduce and/or prevent fluid flow through the lumen 8 of the indwelling medical system 1, and may possibly break loose and enter the host's vasculature. The patency system disclosed herein may be used to remove at least a portion of the debris 7 at any location along the lumen 8 of the indwelling medical system 1, particularly the lumen 8 of either the vascular access port 5 and/or the indwelling catheter 2.

Referring now to FIG. 2, one embodiment of a patency system (e.g., catheter patency system) 10 consistent with the present disclosure is generally illustrated disposed within the indwelling medical system (e.g., indwelling catheter system) 1. At least a portion of the catheter patency system 10 is configured to be disposed within at least a portion of the indwelling catheter system 1 (e.g., the lumen 8 of the indwelling catheter 2 and/or the vascular access port 5 and includes at least one cleaner 12. As explained herein, the catheter patency system 10 may be at least partially withdrawn and/or pulled externally generally in the direction of arrow A such that the cleaner 12 at least partially removes debris 7 from the interior surface 9 of lumen 8 of the indwelling catheter system 1.

Turning now to FIG. 3, one embodiment of a catheter patency system 10 consistent with the present disclosure is generally illustrated. The catheter patency system 10 includes an elongated body (shaft) 14 having a proximal section P, a distal section D, and an intermediate section I disposed between the proximal section P and the distal section D. The elongated body 14 is sized and shaped to be at least partially received within the lumen 8 of the indwelling catheter system 1. The elongated body 14 is formed from one or more materials having sufficient flexible, pushability (i.e., ability to transmit force to the distal portion or tip), and kink resistance to be advanced within bends and contours of the lumen 8 of the indwelling catheter system 1.

According to one embodiment, one or more portions of the elongated body 14 (e.g., the proximal section P, distal section D, and intermediate section I) may have different flexibilities, pushablities, and/or kink resistances. For example, the proximal section P may be more rigid compared to the intermediate section I, and the intermediate section I may be more rigid compared to the distal section D. The distal section D may be the most flexible. One or more of the sections P, I, D may include, for example, a spiral reinforcement and/or or different materials to allow the flexibility, pushability, and kink resistance to be customized and/or selected along the length of the elongated body 14.

The distal section D may optionally include a distal end tip 21 configured to reduce and/or eliminate the potential of the tip 21 from becoming caught in and/or damaging the indwelling catheter system 1, particularly the lumen 8, as the catheter patency system 10 is advanced into and through the lumen 8 of the indwelling catheter system 1. For example, the tip 21 may include a resiliently deformable portion configured to deflect the tip 21 as the catheter patency system 10 is advanced through the lumen 8. According to one embodiment, the tip 21 may include a balloon and/or may have a rounded configuration.

The proximal section P of the elongated body 14 may include a handle 16. The handle 16 may facilitate the gripping of the elongated body 14 by a user (e.g., a surgeon, clinician) when advancing the elongated body 14 of the catheter patency system 10 into and/or out of the lumen 8 of the indwelling catheter system 1 and/or rotating the catheter patency system 10 about the longitudinal axis L. The handle 16 may include, but is not limited to, a T-handle, an area with increased friction (gripability). The handle 16 may also provide a stop member which contacts against the indwelling catheter system 1 to prevent the tip 21 of the catheter patency system 10 from extending into the vasculature (e.g. lumen 4 of the blood vessel). Alternatively (or in addition), the proximal section P may include a coupler portion 18, FIG. 4, configured to be coupled to a separate mechanical, electrical or electro-mechanical rotary driver 20, e.g., a drill. The coupler portion 18 may include a plurality of engagement faces to securely engage and mate with an engagement head 22 of the rotary device, e.g. drill chuck.

As discussed herein, the catheter patency system 10 also includes at least one cleaner 12. While the cleaner 12 is illustrated as being located on at least a portion of the distal section D, it should be appreciated that this is for illustrative purposes only and that one or more of the cleaners 12 may be located along any portion (including the entire length) of the elongated body 14.

According to one embodiment, the cleaner 12 may include one or more cleaning members, such as brushes 24. The brushes 24 may be arranged in any configuration. The configuration may include one or more rows of cleaning elements, such as one or more rows of bristles 26, which may be arranged such that the bristles 26 extending longitudinally along a length of the distal section D. The one or more rows of bristles 26 may also be arranged in a circular (ring) configuration, a spiral configuration and/or a helical configuration. The bristles 26 may be configured to extend generally radially outwardly from the elongated body 14 as protrusions, and may be arranged to provide bumps and/or ridges. The bristles 26 may be formed of the same of different materials. For example, the bristles 26 may include different materials to adjust the stiffness and/or friction.

The bristles 26 may extend radially outwardly from the elongated body 14 (i.e., the radial length R) such that the bristles 26 generally engage and/or contact against a portion of the interior surface 9 (FIG. 2) of the lumen 8 of the indwelling catheter system 1 while the catheter patency system 10 is moved within the lumen 8 of the indwelling catheter system 1 (e.g., the lumen 8). To remove debris 7, the elongated body 14 of the catheter patency system 10 may be advanced generally in the direction of arrow A (FIG. 2) and/or rotated about is longitudinal axis L while within the lumen 8 of the indwelling catheter system 1 (e.g., using with the handle 16 (FIG. 3) and/or the rotary driver 20 (FIG. 4)).

Figure 6:
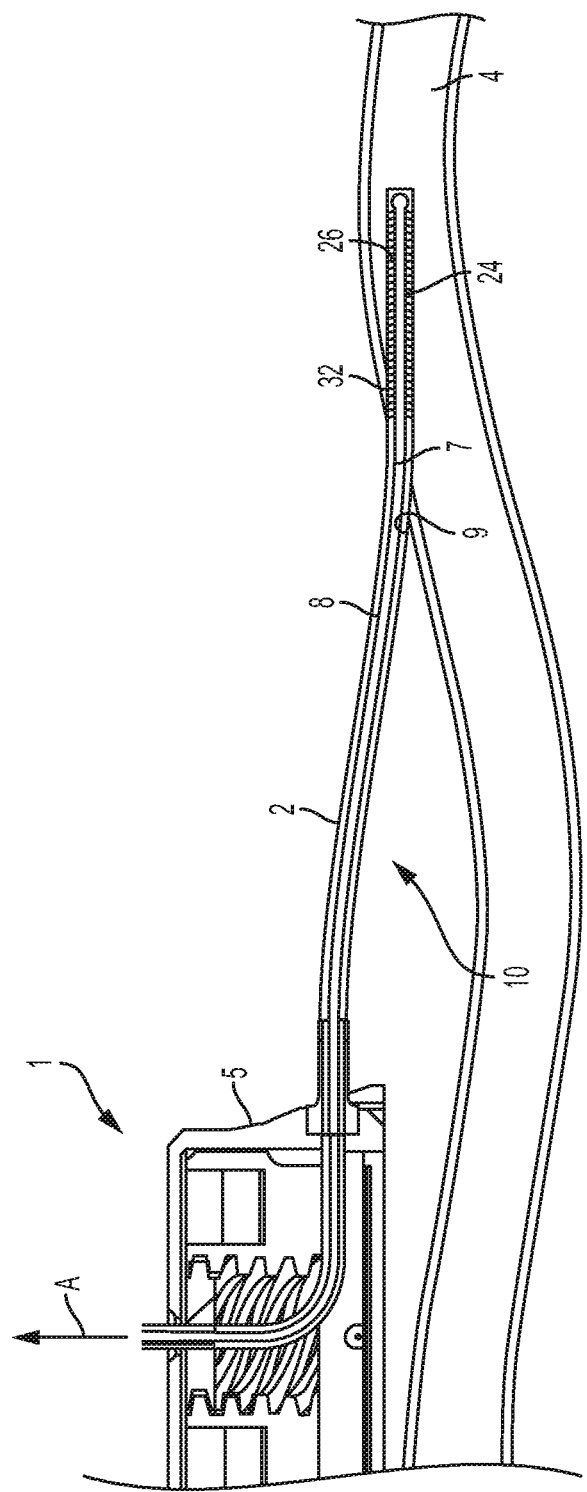
FIG. 6 is a cross-sectional view of another embodiment of a catheter patency system disposed within an indwelling catheter system.

According to one embodiment, the bristles 26 may be configured to be arranged in an expanded position (e.g., as generally illustrated in FIG. 4) and a collapsed or retracted position (as generally illustrated in FIG. 5). In the expanded position (see, for example, FIG. 6), the bristles 26 are arranged extended generally radially outwardly such that the bristles 26 generally engage and/or contact against a portion of the interior surface 9 of the lumen 8 of the indwelling catheter system 1 to remove debris 7. In the collapsed position, the bristles 26 may be arranged generally more towards the elongated body 14 such that the overall cross-section of the catheter patency system 10 (e.g., the diameter) may be reduced.

As may be appreciated, the catheter patency system 10 may be more easily advanced within the lumen 8 of the indwelling catheter system 1 while in the collapsed position compared to the expanded position. Additionally, the catheter patency system 10, when in the collapsed position, is less likely to inadvertently dislodge debris 7 from the lumen 8 of the indwelling catheter system 1 while being advanced into the lumen 8 of the indwelling catheter system 1 (i.e., when the elongated body 14 of the catheter patency system 10 is advanced in the direction generally opposite to arrow A in FIG. 2). As may be appreciated, it may be beneficial to reduce and/or eliminate debris 7 from becoming inadvertently dislodged from the lumen 8 of the indwelling catheter system 1 while advancing the elongated body 14 of the catheter patency system 10 into the lumen 8 of the indwelling catheter system 1 since the inadvertently removed debris 7 may enter into the host's vasculature where it could be deposited elsewhere in the circulatory system, or in the lumen 8 of the catheter system 1, such as in the catheter 2, particularly if there is a valve located in the distal end 3 of the catheter 2.

According to one embodiment, the bristles 26 may be configured to easily bend, collapse, fold, or otherwise move towards the elongated body 14 into the collapsed position as the catheter patency system 10 is advanced into the lumen 8 of the indwelling catheter system 1, and extend radially outwardly into the expanded position when the catheter patency system 10 is advanced out of the lumen 8 of the indwelling catheter system 1 (e.g., withdrawn from the indwelling catheter patency system 10 generally in the direction of arrow A in FIG. 2). For example, the bristles 26 may have a limited range of motion.

According to another embodiment, the catheter patency system 10 may include a position selector 28 (FIG. 5). The position selector 28 may be configured to allow the user to articulate the cleaner 12 between the collapsed and expanded positions (or any position therebetween). For example, the position selector 28 may include a switch, tab or slider coupled to the bristles 26 that urges the bristles 26 generally radially outwardly and inwardly. The user may push the position selector 28 to select between the expanded and collapsed positions, such as by moving the position selector 28 distally to expand the bristles 28 and moving the position selector proximally to contract the bristles 26. In at least one embodiment, the bristles 26 may at least partially retract into a portion of the elongated body 14.

Figure 7:
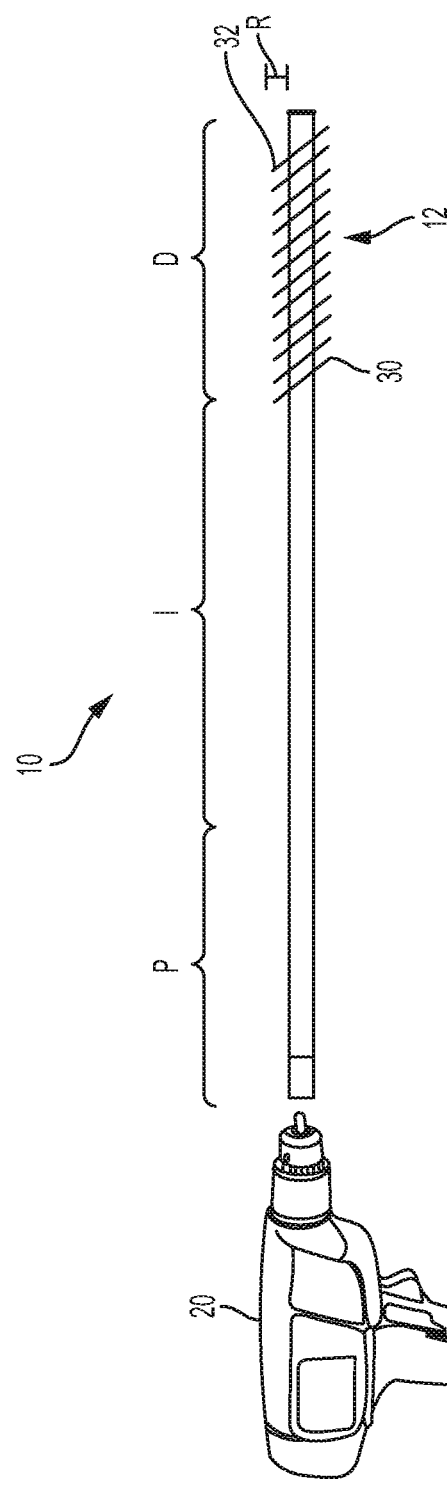
FIG. 7 is a cross-sectional view of another embodiment of a catheter patency system consistent with the present disclosure.
Figure 8:
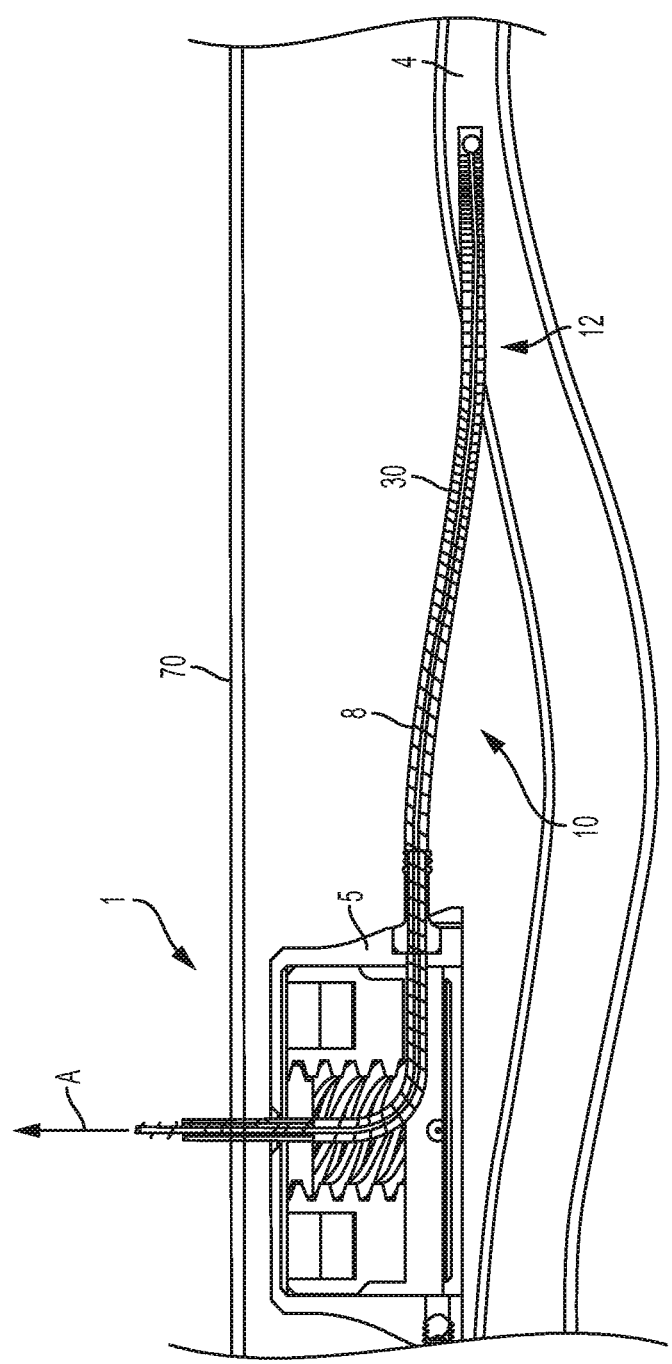
FIG. 8 is a cross-sectional view of another embodiment of a catheter patency system disposed within an indwelling catheter system.

Turning now to FIGS. 7 and 8, another embodiment of the cleaner 12 is generally illustrated. The cleaner 12 may include one or more augers 30. The augers 30 may include one or more flanges 32 extending generally radially outwardly from the elongated body 14 having a generally spiral configuration, helical configuration, and/or an arcuate configuration. The flanges 32 may extend completely or partially around the periphery and/or circumference of the elongated body 14 and may be made from a resiliently deformable material. The radial length R of the flanges 32 may be selected such that the augers 30 generally engage and/or contact against a portion of the interior surface 9 (FIG. 8) of the indwelling catheter system 1 while the catheter patency system 10 is moved within the lumen 8 of the indwelling catheter system 1. The auger 30 may extend along any portion of the elongated body 14, for example, the distal section D as generally illustrated in FIG. 7 and/or along substantially the entire length of the elongated body 14 as generally illustrated in FIG. 8.

To remove debris 7, the catheter patency system 10 may be rotated as described herein. The rotation of the auger 30 causes debris 7 to be dislodged from the interior surface 9 of the indwelling catheter system 1. Additionally, rotation of the auger 30 causes dislodged debris 7 to be urged proximally (e.g., generally away from the distal section D and generally towards the proximal section P), thereby reducing and/or eliminating the potential for dislodged debris 7 to exit the indwelling catheter system 1 and enter into the host's circulatory system or be lodged elsewhere in the indwelling catheter system 1.

Figure 9:
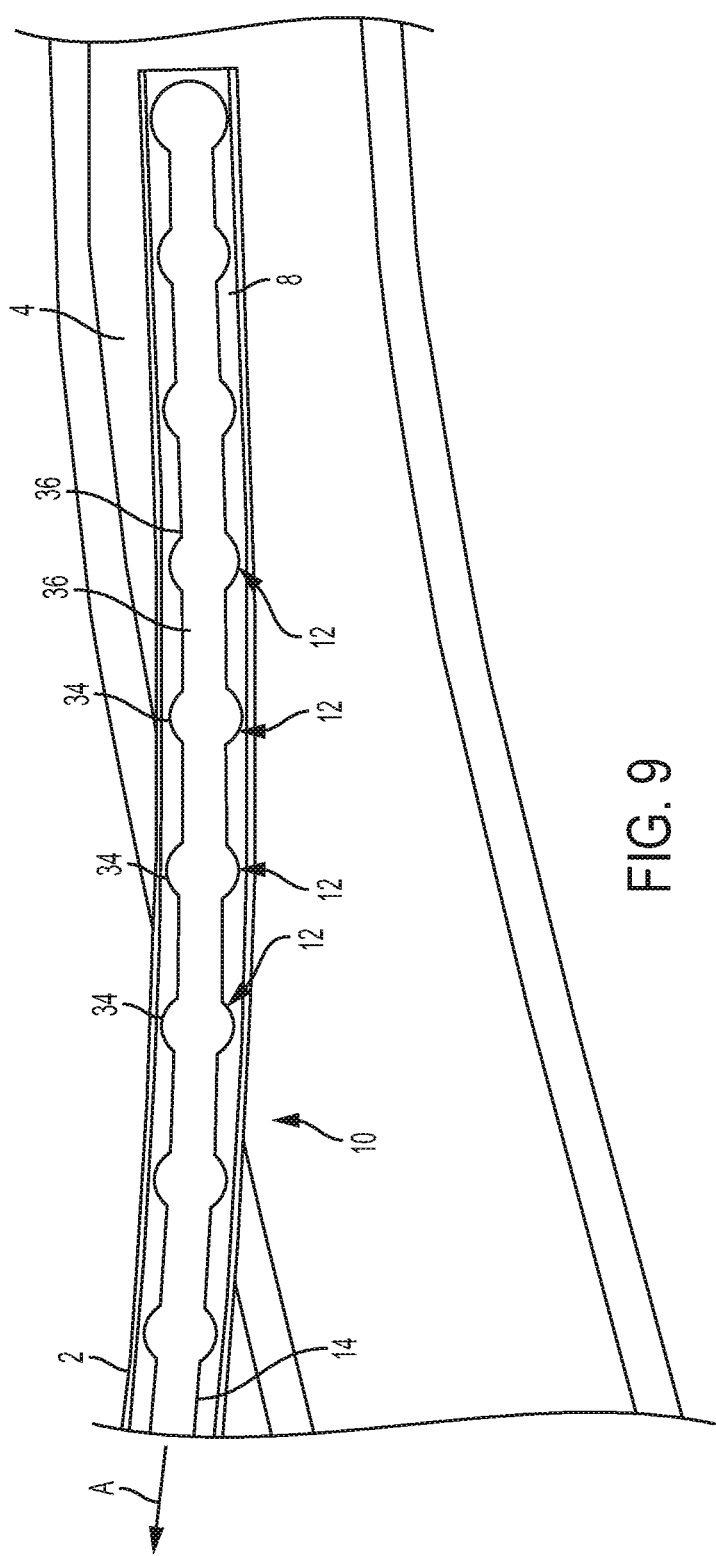
FIG. 9 is a cross-sectional view of a another embodiment of a catheter patency system consistent with the present disclosure.
Figure 10:
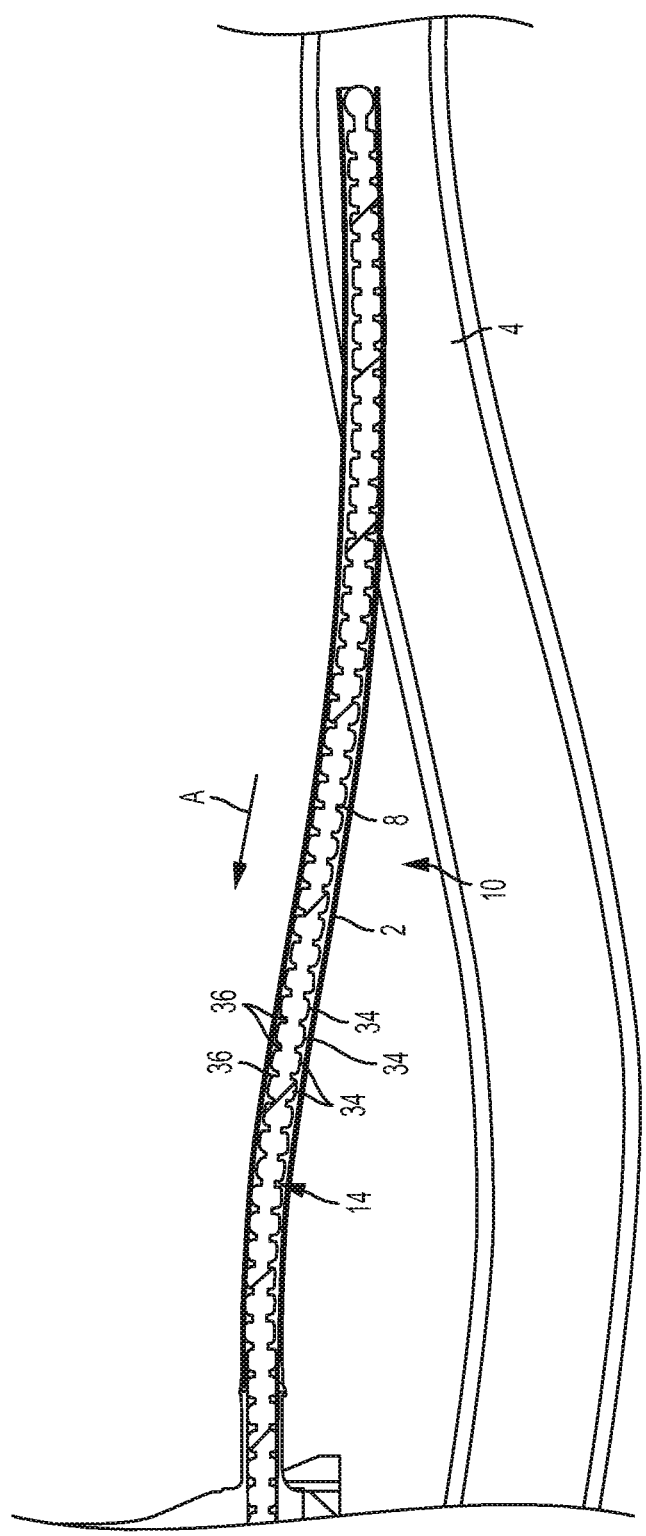
FIG. 10 is a cross-sectional view of another embodiment of a catheter patency system consistent with the present disclosure.
Figure 11:
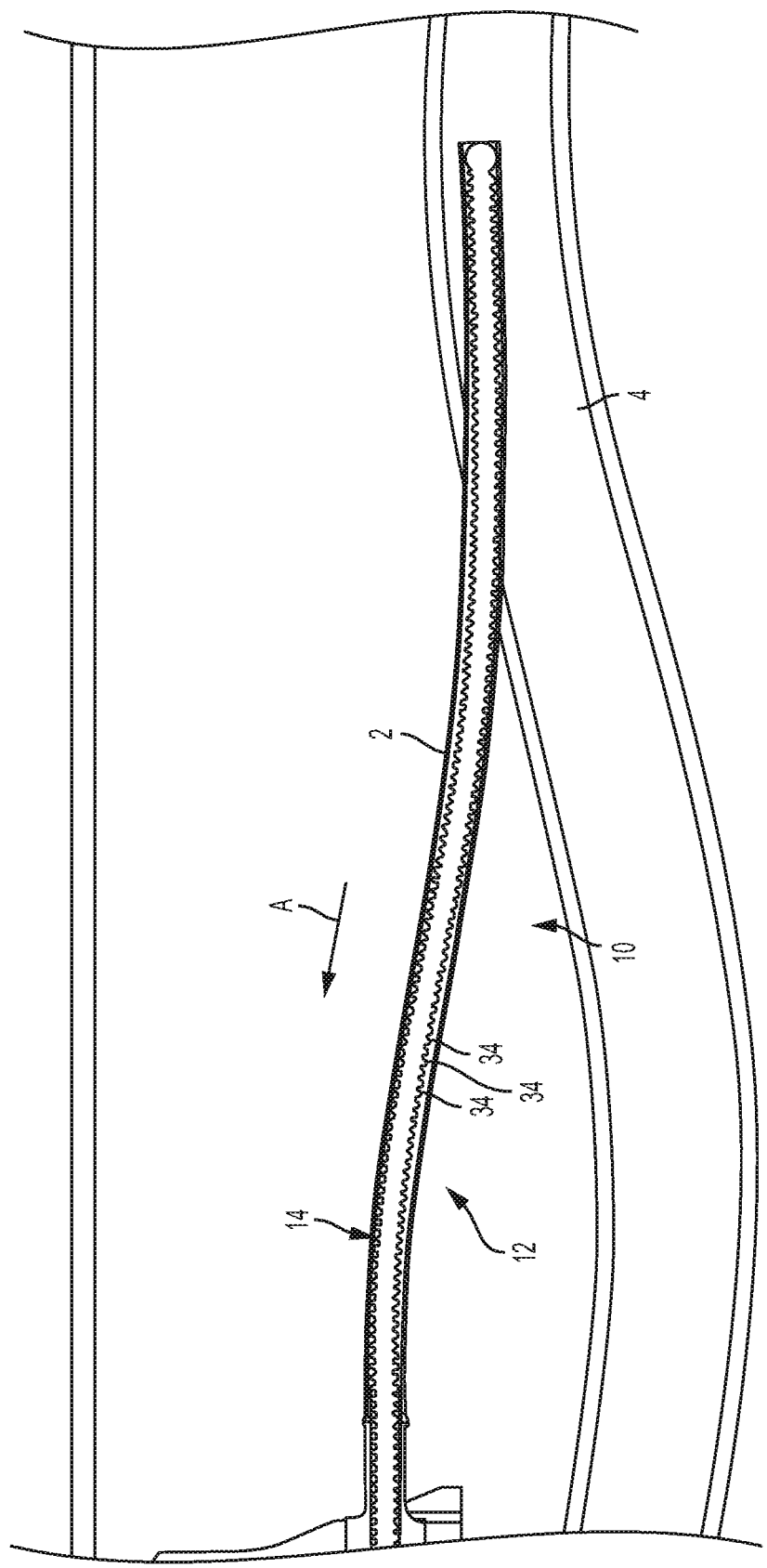
FIG. 11 is a cross-sectional view of another embodiment of a catheter patency system consistent with the present disclosure.

With reference to FIGS. 9-11, yet another embodiment of the cleaner 12 is generally illustrated. The cleaner 12 may include one or more protrusions 34 (e.g. bumps, flanges ribs) extending generally radially outwardly from the elongated body 14. For example, the protrusions 34 may have a generally spherical and/or hemispherical configuration as generally illustrated in FIG. 9, a generally ring and/or ridged configuration as generally illustrated in FIG. 10, and/or a knurled portion as generally illustrated in FIG. 11. The protrusions 34 may have a radial length R selected such that the protrusions 34 generally engage and/or contact against a portion of the interior surface 9 (FIG. 8) of the lumen 8 of the indwelling catheter system 1 while the catheter patency system 10 is moved within the lumen 8 of the indwelling catheter system. The protrusions 34 may be separated by flexible segments 36. To remove debris 7, the elongated body/shaft 14 of the catheter patency system 10 may be advanced generally in the direction of arrow A and/or rotated about is longitudinal axis L while within the lumen 8 of the indwelling catheter system 1 (e.g., using with the handle 16 (FIG. 3) and/or the rotary driver 20 (FIG. 4)).

Figure 12:
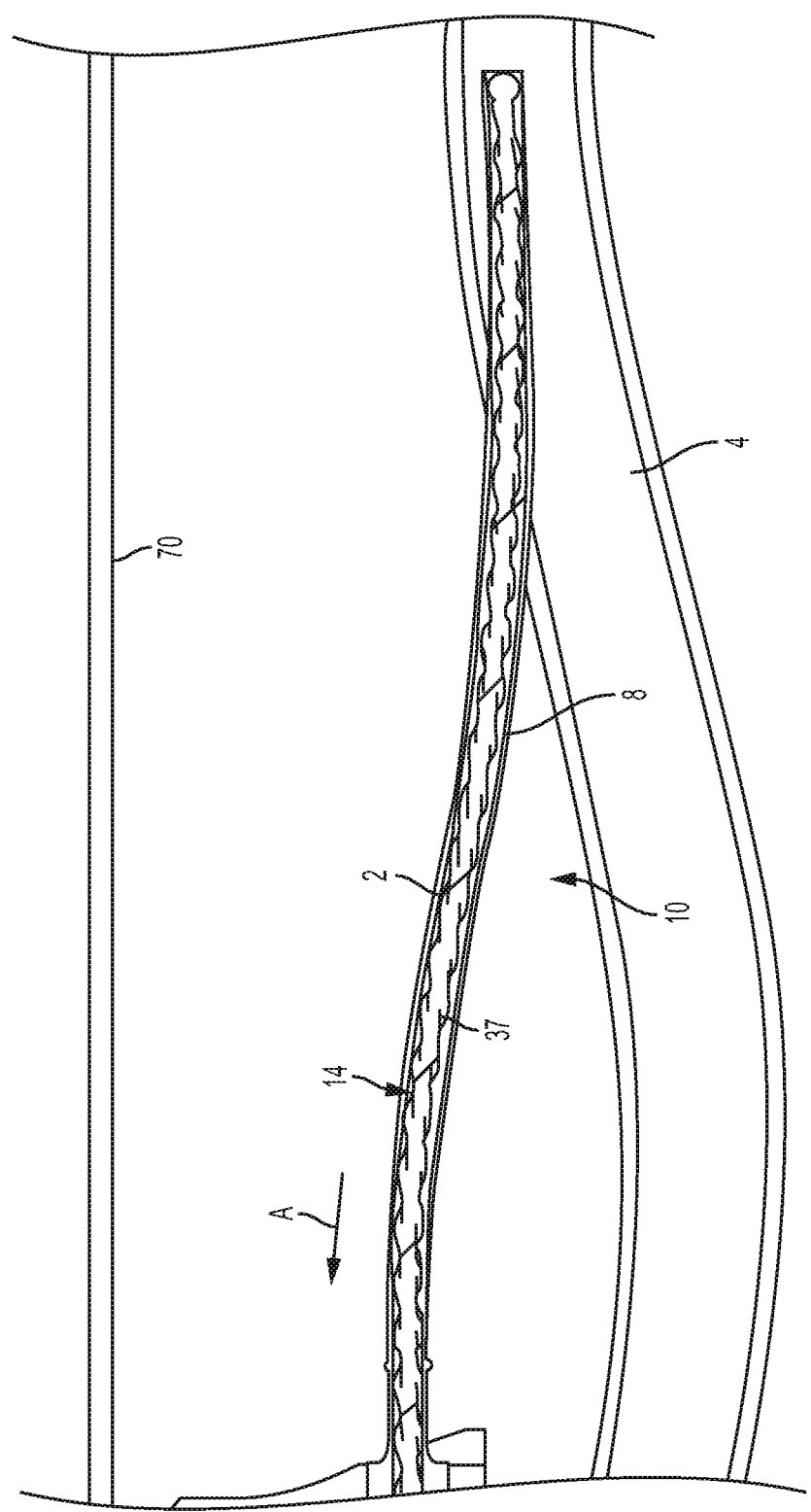
FIG. 12 is a cross-sectional view of another embodiment of a catheter patency system consistent with the present disclosure.

According to yet another embodiment as shown in FIG. 12, the cleaner 12 may include a one or more strands 37 configured to form an abrasive surface configured to dislodge debris 7 from the lumen 8 of the indwelling catheter system 1. For example, a single strand 37 may be twisted. Alternatively, a plurality of strands may be twisted, woven or braided. Similar to other embodiments, the elongated body 14 of the catheter patency system 10 may be advanced generally in the direction of arrow A and/or rotated about is longitudinal axis L while within the lumen 8 of the indwelling catheter system 1 (e.g., using with the handle 16 (FIG. 3) and/or the rotary driver 20 (FIG. 4)) to remove debris 7.

Figure 13:
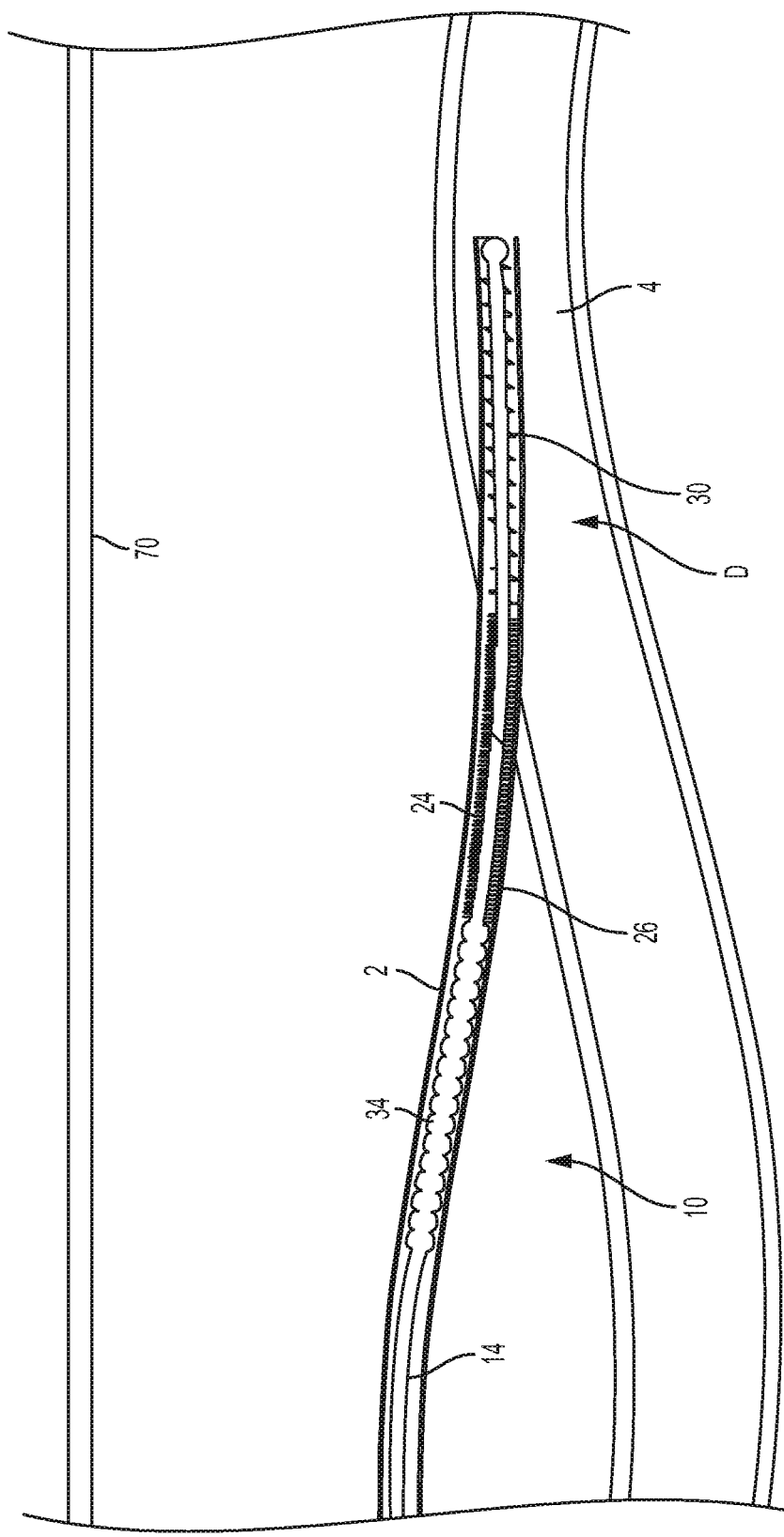
FIG. 13 is a cross-sectional view of another embodiment of a catheter patency system consistent with the present disclosure.

It should be appreciated that the catheter patency system 10 is not limited to each individual type of cleaner 12 described herein. Additionally, the catheter patency system 10 may include a plurality of cleaners 12. For example, as shown in FIG. 13, the catheter patency system 10 may include one or more protrusions 34, one or more brushes 24, and/or one or more augers 30. For example, the elongated body 14 may include a plurality of protrusion 34 and bristles 26 configured to dislodge debris 7 (not shown for clarity). An auger 30 may be located distally from the protrusions 34 and bristles 26, and may be configured to urge dislodged debris 7 proximally (thereby reducing and/or eliminating dislodged debris 7 from entering into the host's circulatory system or being lodged elsewhere in indwelling catheter system 1). However, this is just an example, and other configurations are within the scope of the present disclosure.

Figure 14:
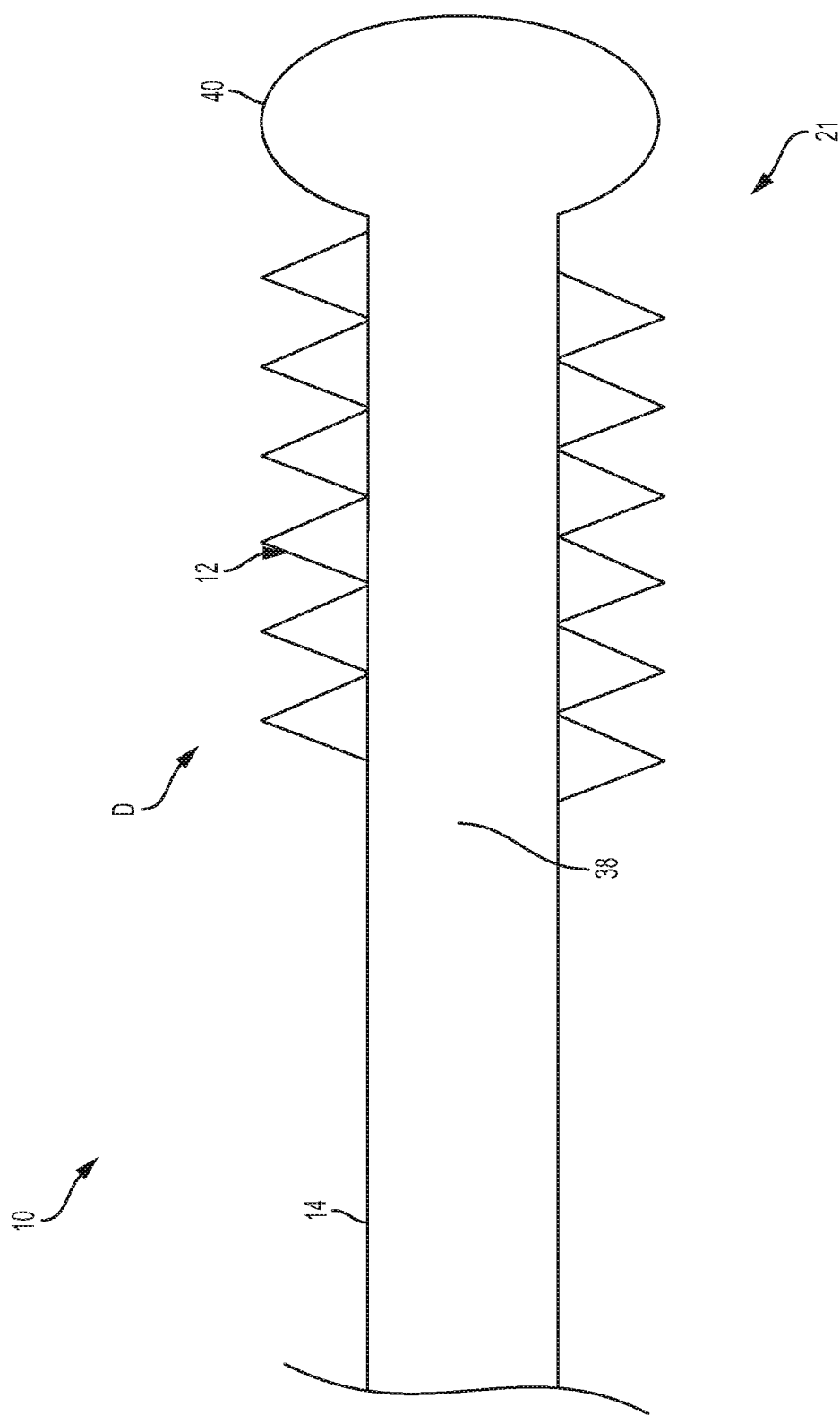
FIG. 14 is a cross-sectional view of an embodiment of a catheter patency system having a balloon consistent with the present disclosure.
Figure 15:
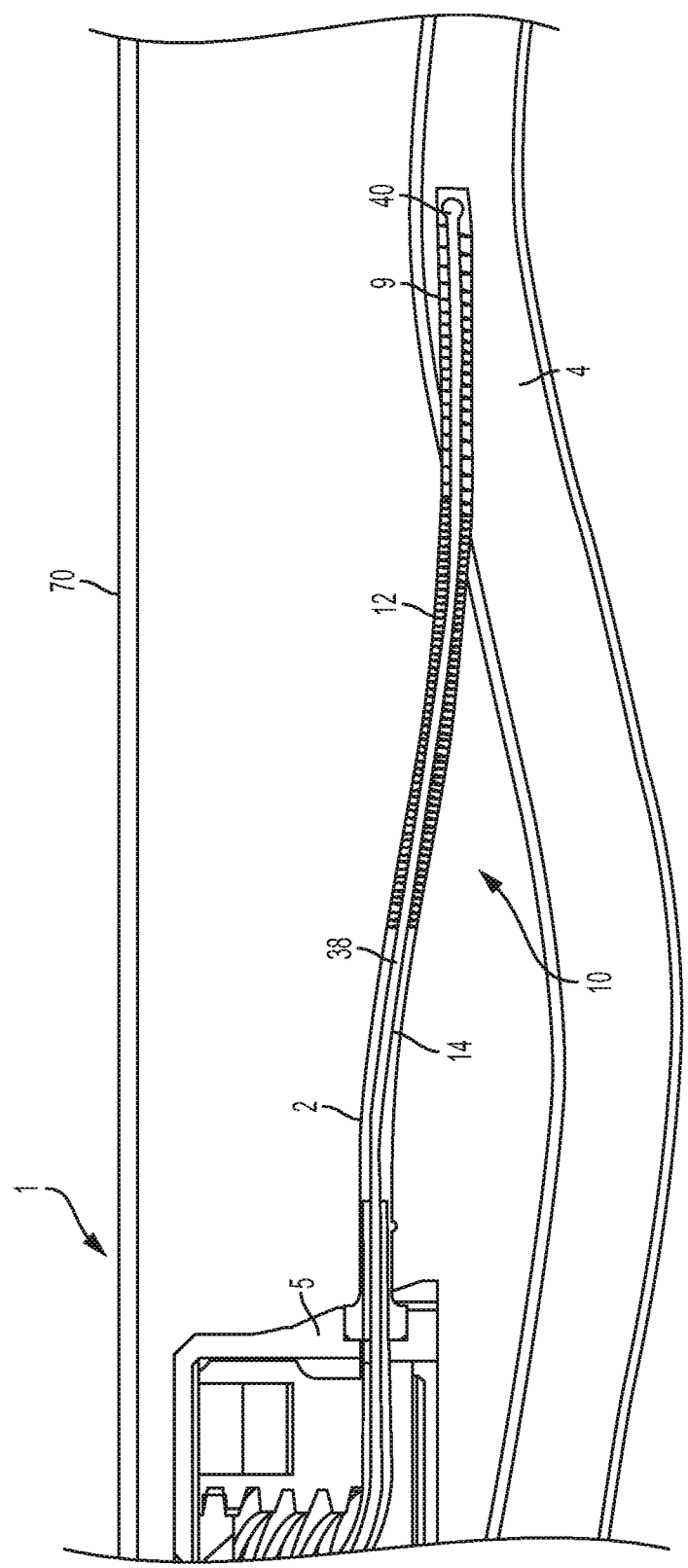
FIG. 15 is a cross-sectional view of an embodiment of a catheter patency system having a balloon disposed within an indwelling catheter system consistent with the present disclosure.

Turning now to FIGS. 14-16, another embodiment of the catheter patency system 10 is generally illustrated. The catheter patency system 10 includes an elongated body 14 defining at least one lumen 38 and an inflatable balloon 40. According to one embodiment, the lumen 38 may include an inflation lumen configured to at least partially inflate the balloon 40. For example, the balloon 40 may be coupled to the tip 21 of the elongated body 14 and in fluid communication with the inflation lumen 38 as generally illustrated in FIG. 14. The opposite end of the inflation lumen 38 may be configured to be coupled to an inflation fluid source (e.g., a source of saline, water, heparin, contrast fluid, which is not shown for clarity) to inflate the balloon 40.

Figure 16A:
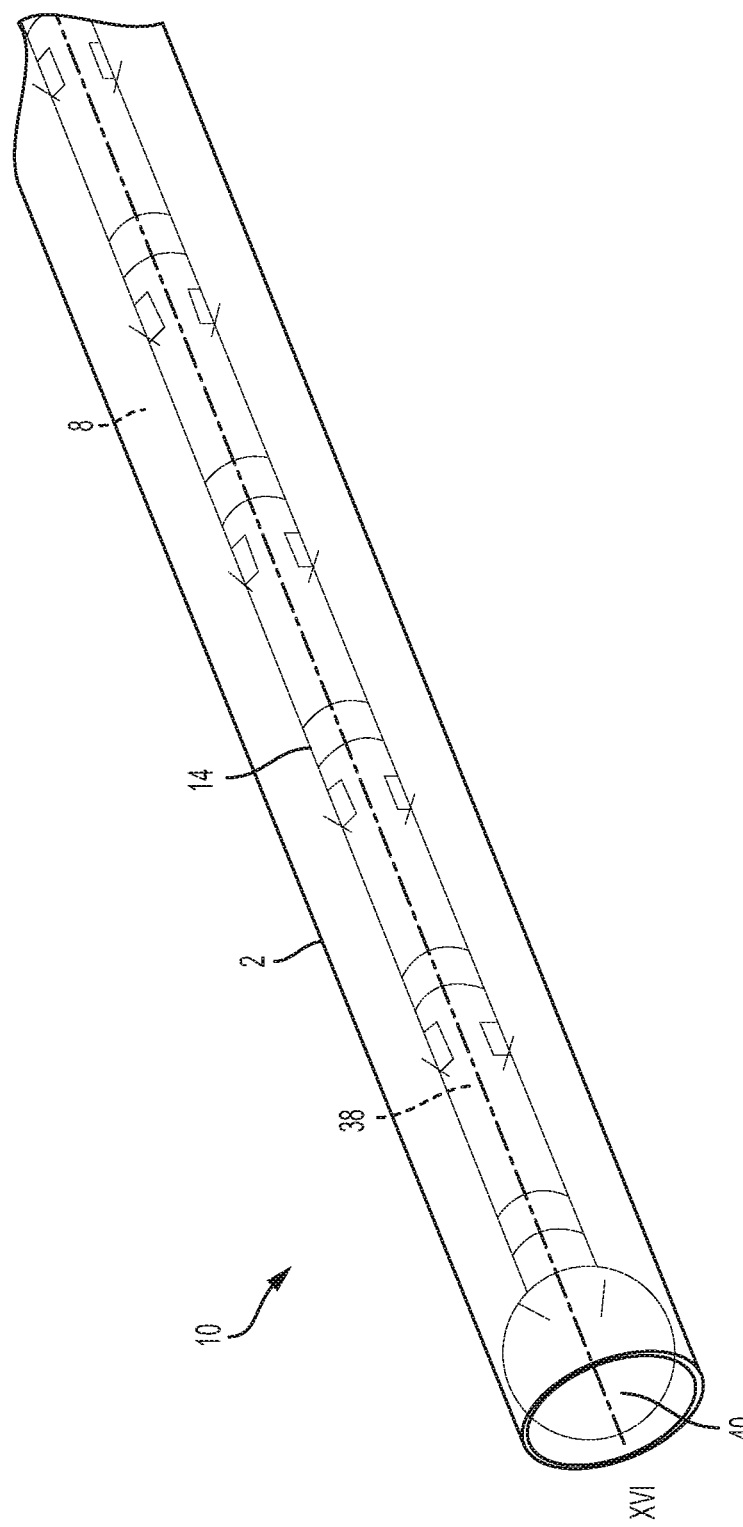
FIG. 16A is a view of an embodiment of a catheter patency system having a balloon consistent with the present disclosure.
Figure 16B:
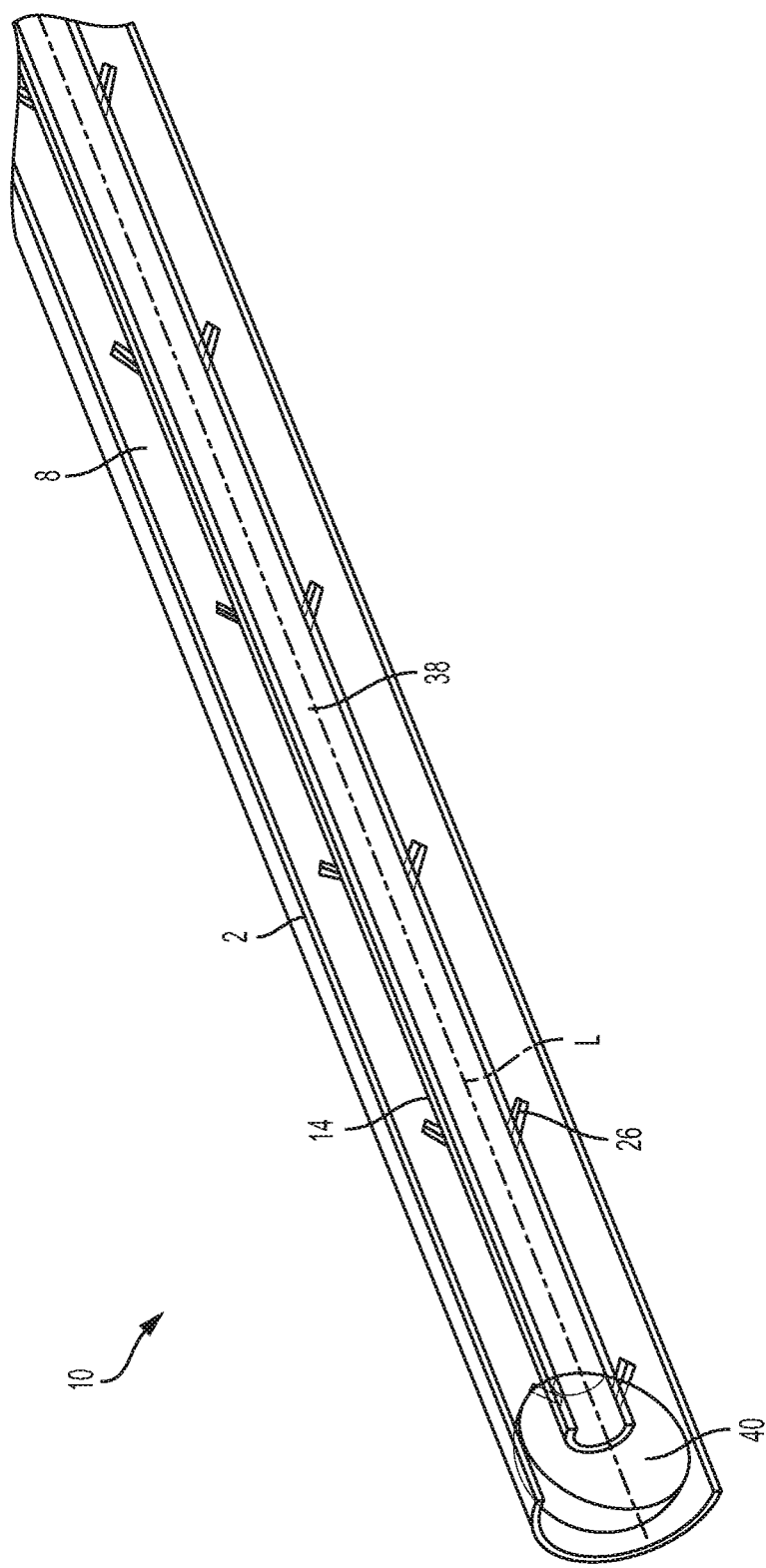
FIG. 16B is a cross-sectional view of the catheter patency system of FIG. 16A taken along line XVI-XVI.

In practice, elongated body 14 of the catheter patency system 10 may be advanced into the lumen 8 of the indwelling catheter system 1 while the balloon 40 is deflated (or at least partially deflated). To remove debris 7, the balloon 40 may be inflated via the inflation lumen 38 such that the balloon 40 contacts the interior surface 9 of the lumen 8 of the indwelling catheter system 1 as generally illustrated in FIGS. 15, 16A, and 16B.

According to at least one embodiment, the balloon 40 may generally form a seal with the interior surface 9 of the lumen 8 to thereby preventing dislodged debris 7 from exiting the indwelling catheter system 1 and entering into the host's circulatory system. The catheter patency system 10 may be advanced generally in the direction of arrow A and/or rotated about is longitudinal axis L while within the lumen 8 of the indwelling catheter system 1 (e.g., using with the handle 16 (FIG. 3) and/or the rotary driver 20 (FIG. 4)) such that the cleaner 12 dislodges debris 7 as discussed herein. The dislodged debris 7 may be removed from the indwelling catheter system 1, for example, using a vacuum source as discussed herein. Alternatively, while inflated, the balloon 40 may be retracted proximally within lumen 8, during which time the balloon 40 may scrape the interior surface 9 of the lumen 8 to remove more debris 7, as well as pull debris 7 out of the lumen 8.

Figure 17:
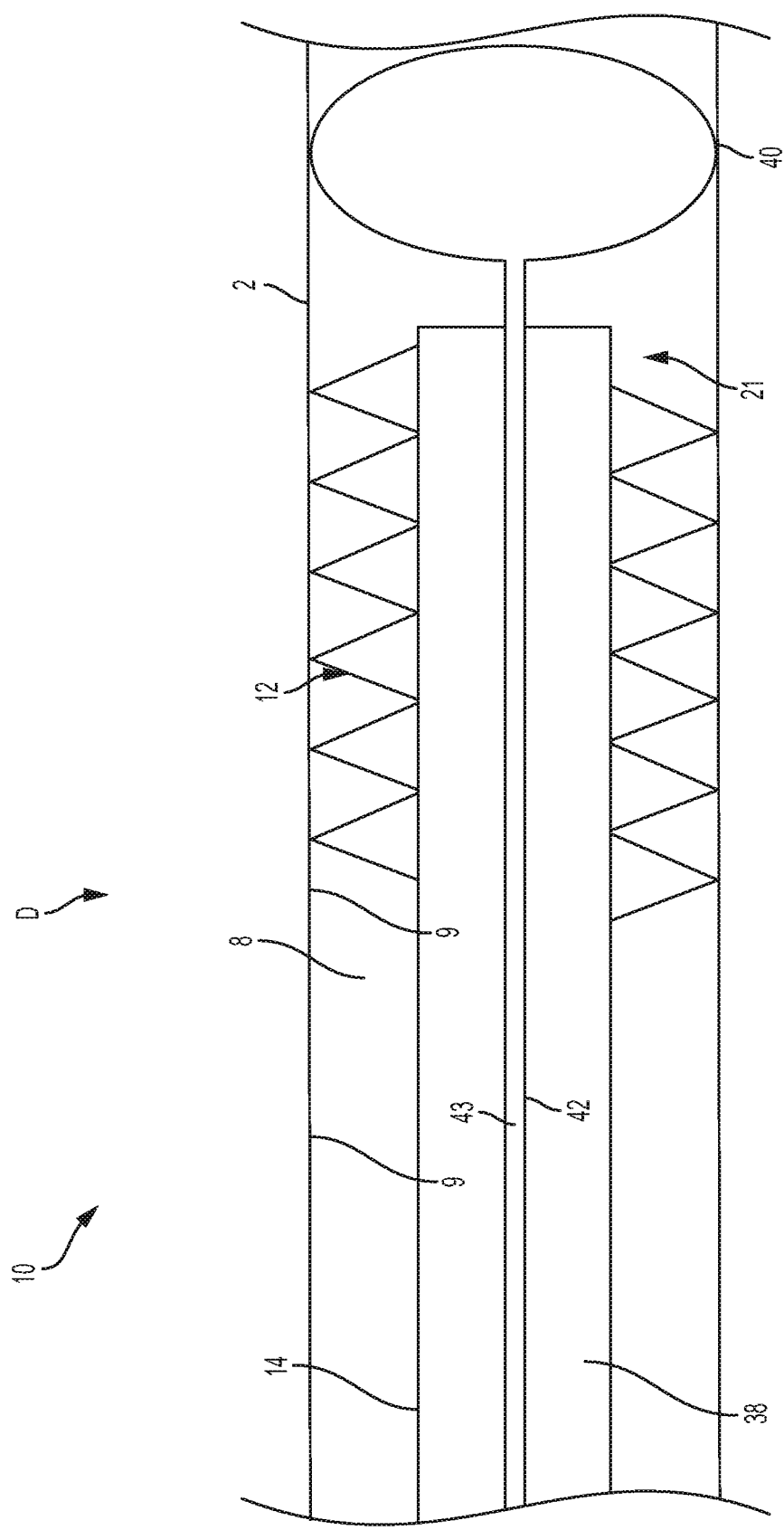
FIG. 17 is a cross-sectional view of another embodiment of a catheter patency system having a balloon consistent with the present disclosure.

Turning now to FIG. 17, another embodiment of the catheter patency system 10 is generally illustrated. Similar to FIGS. 14-16, the catheter patency system 10, FIG. 17, includes an elongated body 14 defining at least one lumen 38, and includes a balloon 40. An elongated, cannulated balloon shaft 42 is fluidly coupled to the balloon 40 and a fluid source (not shown for clarity). The cannulated balloon shaft 42 (and optionally the balloon 40) is configured to be at least partially received within the lumen 38 (e.g., balloon lumen 38).

In practice, the cannulated balloon shaft 42 (and optionally the balloon 40) may be at least partially received within the lumen 38 of the catheter patency system 10 may be advanced into the lumen 8 of the indwelling catheter system 1. The balloon 40 may optionally be deflated (or at least partially deflated). To remove debris 7, the balloon 40 may be inflated via a lumen 43 of the cannulated balloon shaft 42 such that the balloon 40 is advanced outwardly from the elongated body 14, for example, beyond the tip 21. The inflated balloon 40 may contact the interior surface 9 of the lumen 8 of the indwelling catheter system 1 such that the balloon 40 generally forms a seal with the interior surface 9, thereby preventing dislodged debris 7 from exiting the indwelling catheter system 1 and entering into the host's circulatory system. The elongated body 14 and the cleaner 12 of the catheter patency system 10 may be advanced generally in the direction of arrow A and/or rotated about is longitudinal axis L while within the indwelling catheter system 1 (e.g., using with the handle 16 (FIG. 3) and/or the rotary driver 20 (FIG. 4)) such that the cleaner 12 dislodges debris 7 as discussed herein. The inflated balloon 40 may remain stationary while the elongated body 14 and cleaner 12 are withdrawn. The dislodged debris 7 may be removed from the indwelling catheter system 1, for example, using a vacuum source as discussed herein.

Figure 18:
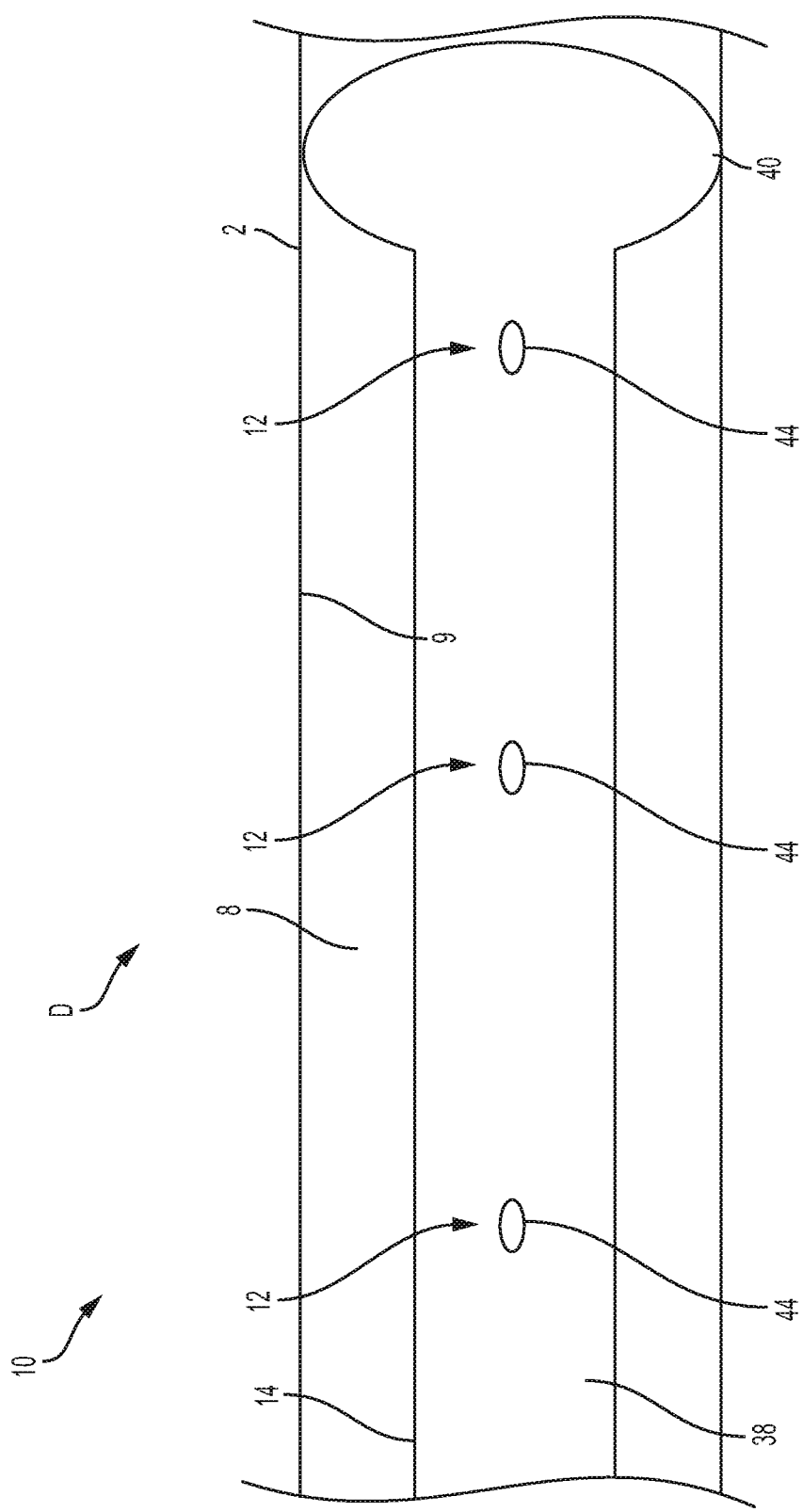
FIG. 18 is a cross-sectional view of another embodiment of a catheter patency system having a balloon consistent with the present disclosure.

Referring now to FIG. 18, a further embodiment of the catheter patency system 10 is generally illustrated. The catheter patency system 10 may include an elongated body 14 defining at least one lumen 38 (e.g., fluid lumen) fluidly coupled to a fluid source (not shown for clarity) as well as a balloon 40 and one or more cleaners 12. The cleaners 12 may comprise fluid jets, nozzles, and/or flushing ports 44. In practice, the fluid lumen 38 may be coupled to a pressurized fluid source to supply fluid to at least partially inflate the balloon 40 such that the balloon 40 contacts the interior surface 9 of the lumen 8 of the indwelling catheter system 1 to generally form a seal with the interior surface 9, thereby preventing dislodged debris 7 from exiting the indwelling catheter system 1 and entering into the host's circulatory system. The pressurized fluid is also ejected from the ports 44 with sufficient force to at least partially dislodge debris 7 from the interior surface 9 of the lumen 8 of the indwelling catheter system 1. The dislodged debris 7 may be removed from the indwelling catheter system 1, for example, using a vacuum source as discussed herein.

Figure 19:
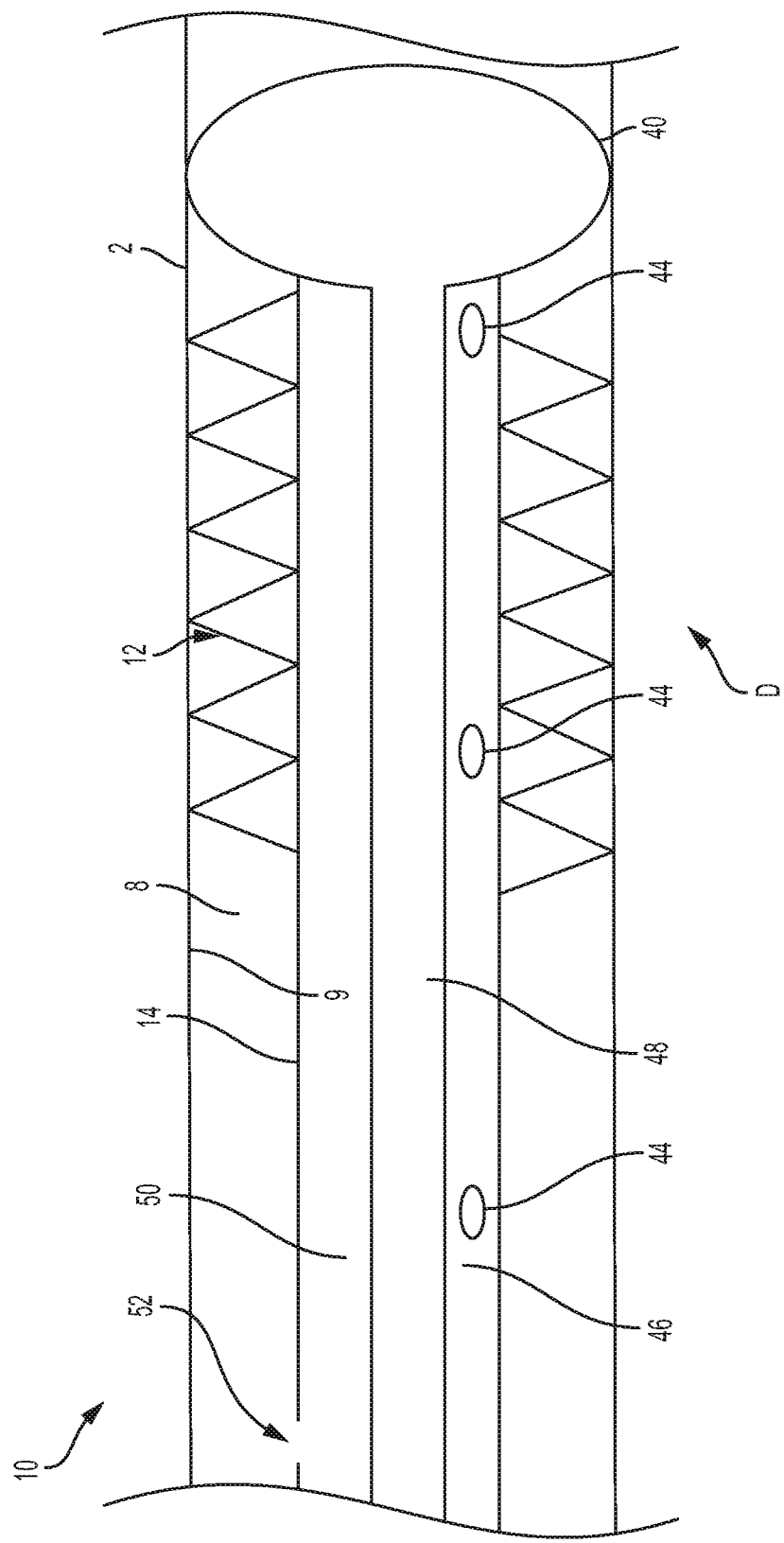
FIG. 19 is a cross-sectional view of another embodiment of a catheter patency system having a balloon consistent with the present disclosure.

Turning to FIG. 19, the catheter patency system 10 may include an elongated body 14 featuring a plurality of lumens, and optionally a balloon 40. For example, the elongated body 14 may include a flushing lumen 46 in fluid communication with a pressurized fluid source (not shown for clarity) and one or more fluid jets, nozzles, and/or flushing ports 44 (and optionally the balloon 40), optionally a separate balloon lumen 48 in fluid communication with a pressurized fluid source (not shown for clarity) and the balloon 40, and optionally a vacuum lumen 50 in fluid communication with a vacuum source (not shown for clarity) and one or more vacuum ports, apertures or openings 52. The cleaner 12 may include any cleaner described herein (e.g., but not limited to, bristles, augur, protrusions, and fluid jets).

Figure 20:
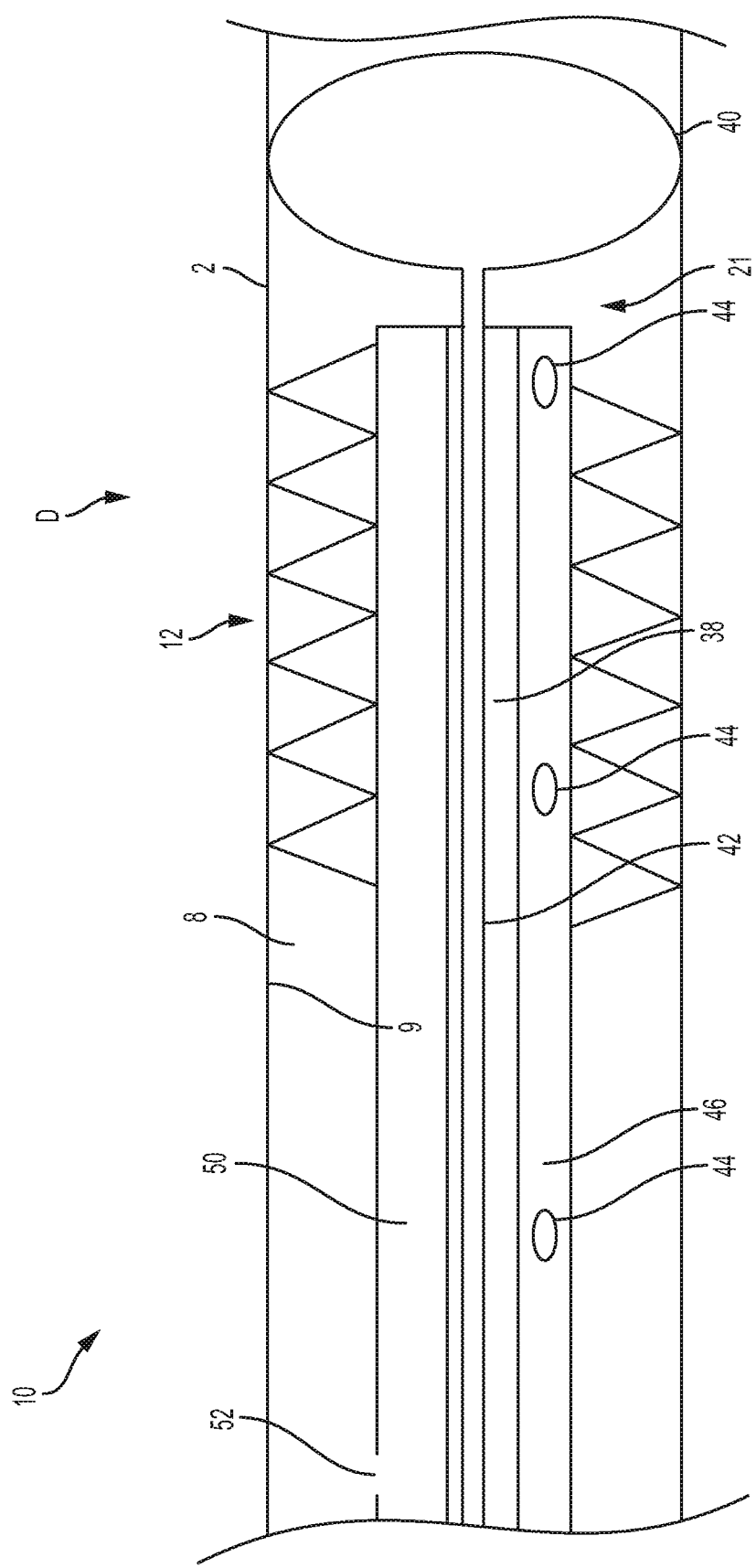
FIG. 20 is a cross-sectional view of another embodiment of a catheter patency system having a balloon consistent with the present disclosure.
Figure 21:
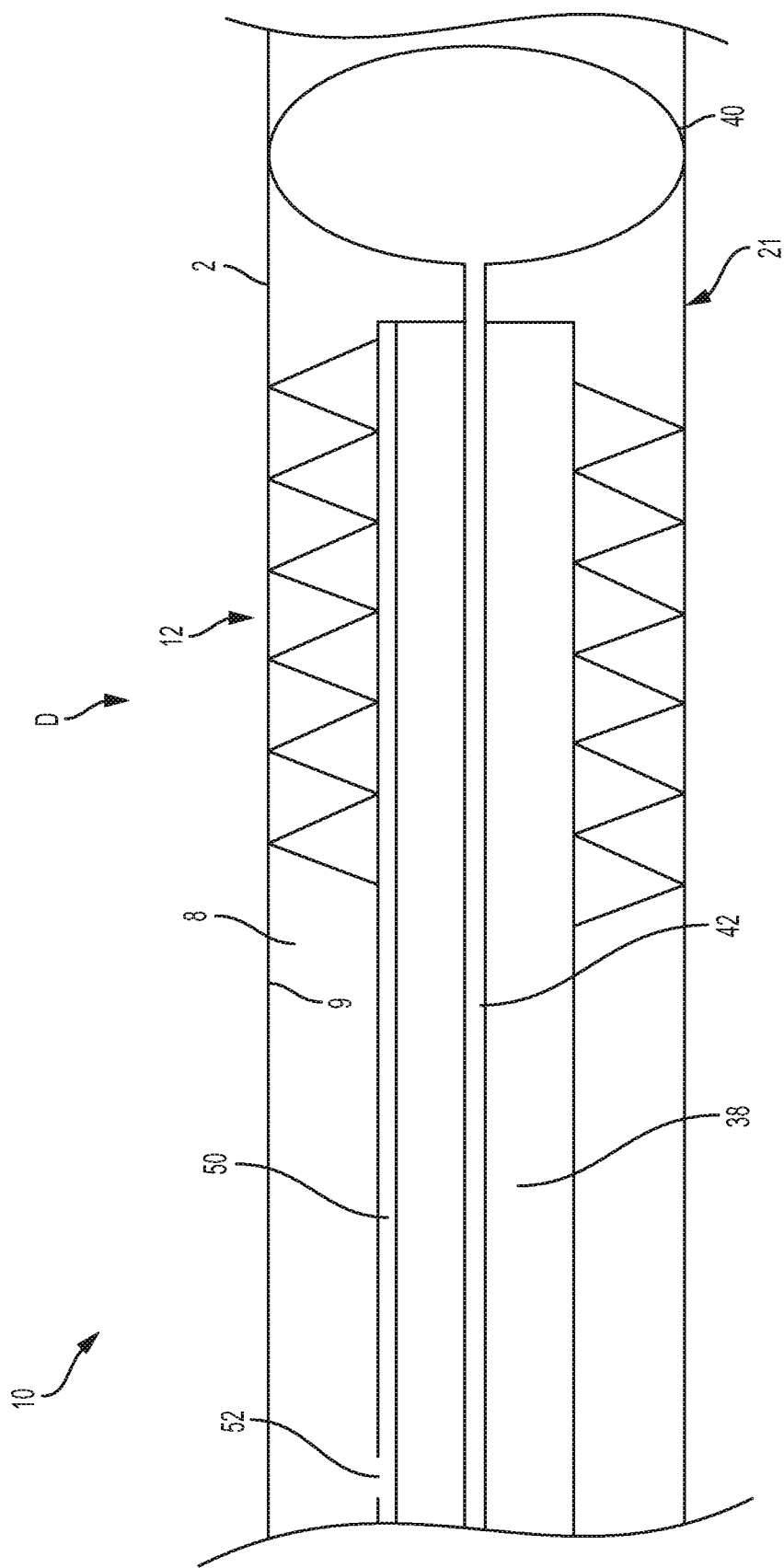
FIG. 21 is a cross-sectional view of another embodiment of a catheter patency system having a balloon consistent with the present disclosure.

Similar to FIG. 19, the catheter patency systems 10, FIG. 20-21, may include a balloon 40 having an elongated, cannulated balloon shaft 42 fluidly coupled to the balloon 40 and a fluid source (not shown for clarity). The cannulated balloon shaft 42 (and optionally the balloon 40) is configured to be moveably disposed within at least partially received within a balloon lumen 38 similar to catheter patency system 10 of FIG. 17. In the embodiment of FIG. 20, the cannulated balloon shaft 42 (and optionally the balloon 40) is configured to be movably disposed within a balloon lumen 38. In the embodiment of FIG. 21, the balloon lumen 38 may optionally be coupled to a fluid source (not shown for clarity), for example to provide a flushing fluid to aid in moving the dislodged debris 7 towards the vacuum ports 52 and into the vacuum lumen 50.

Consistent with other embodiments described herein, the cleaner(s) 12 (FIGS. 19-21) are configured to dislodge debris 7 and the balloon 40 may generally prevent dislodged debris 7 from exiting the indwelling catheter system 1 and entering into the host's circulatory system. Dislodged debris 7 may be removed from the indwelling catheter system 1 via the vacuum ports 52 and vacuum lumen 50. Optionally, the dislodged debris 7 may be removed with the aid of fluid from the flushing lumen 46 and/or balloon lumen(s) 38, 48.

Figure 22:
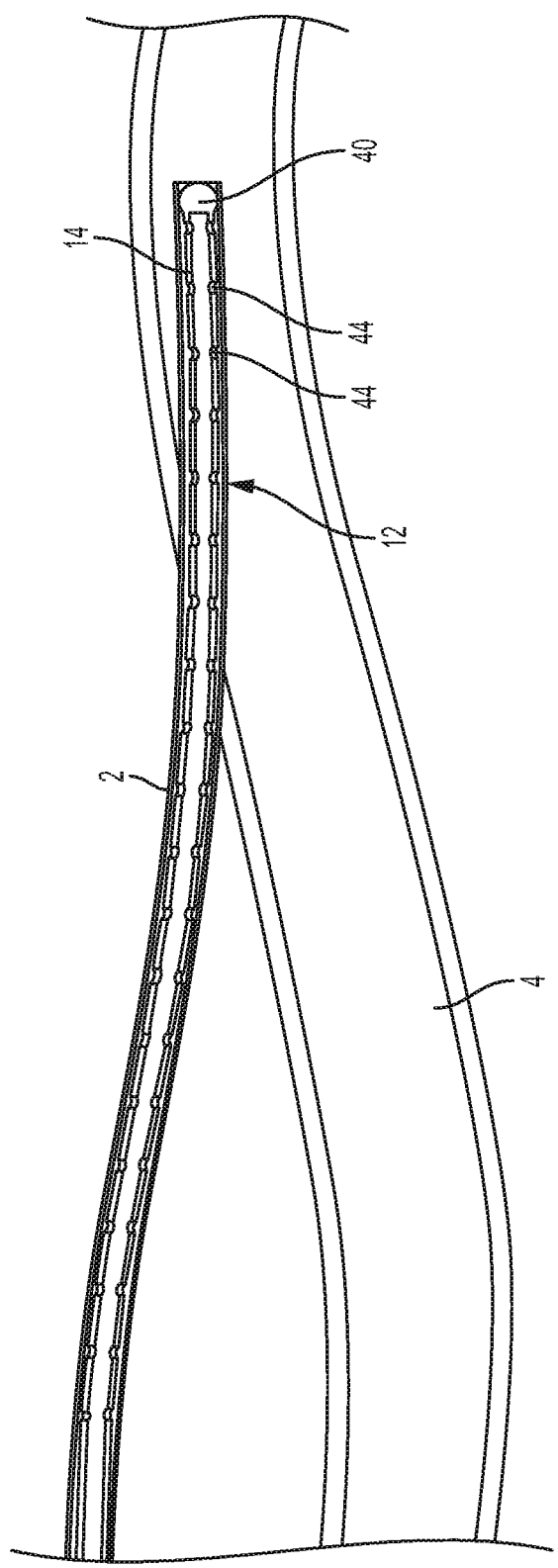
FIG. 22 is a cross-sectional view of another embodiment of a catheter patency system having a balloon disposed within an indwelling catheter system consistent with the present disclosure.

Turning now to FIG. 22, the catheter patency system 10 may include a balloon 40 as described herein, and one or more cleaners 12 in the form of one or more fluid jets, nozzles, and/or flushing ports 44. The ports 44 may be configured to eject fluid to dislodge debris 7 (e.g., but not limited to, pressurized fluid and/or fluid to at least partially dissolve and/or break-up debris) as described herein. The indwelling catheter system 1 may be coupled to a vacuum source (not shown for clarity) to remove the dislodged debris 7.

Figure 23:
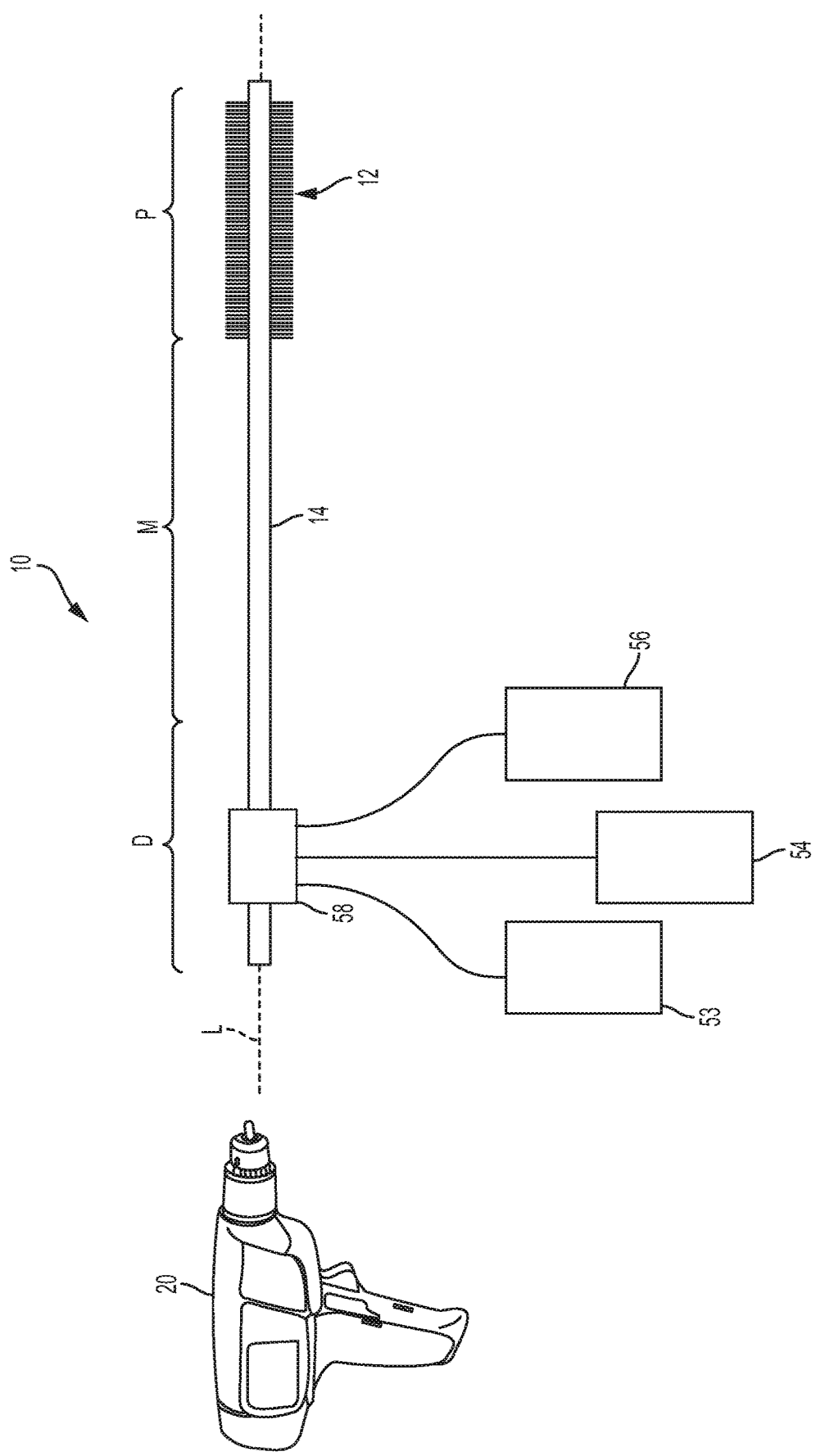
FIG. 23 is a cross-sectional view of an embodiment of a catheter patency system having a coupler consistent with the present disclosure.

With reference to FIG. 23, one embodiment of the catheter patency system 10 is shown coupled with one or more fluid sources 52, inflation sources 54, and/or vacuum sources 56. One or more of the fluid sources 53, inflation sources 54, and/or vacuum sources 56 may be coupled to the elongated body 14 using a coupler 58. The coupler 58 may be configured to allow the elongated body 14 to rotate along its longitudinal axis L, while the fluid sources 53, inflation sources 54, and/or vacuum sources 56 remain substantially stationary. According to one embodiment, the coupler 58 may include a hemostatic valve/port (e.g., a rotating hemostatic valve); however, the catheter patency system 10 may be used with other types of couplers known to those skilled in the art.

Figure 24:
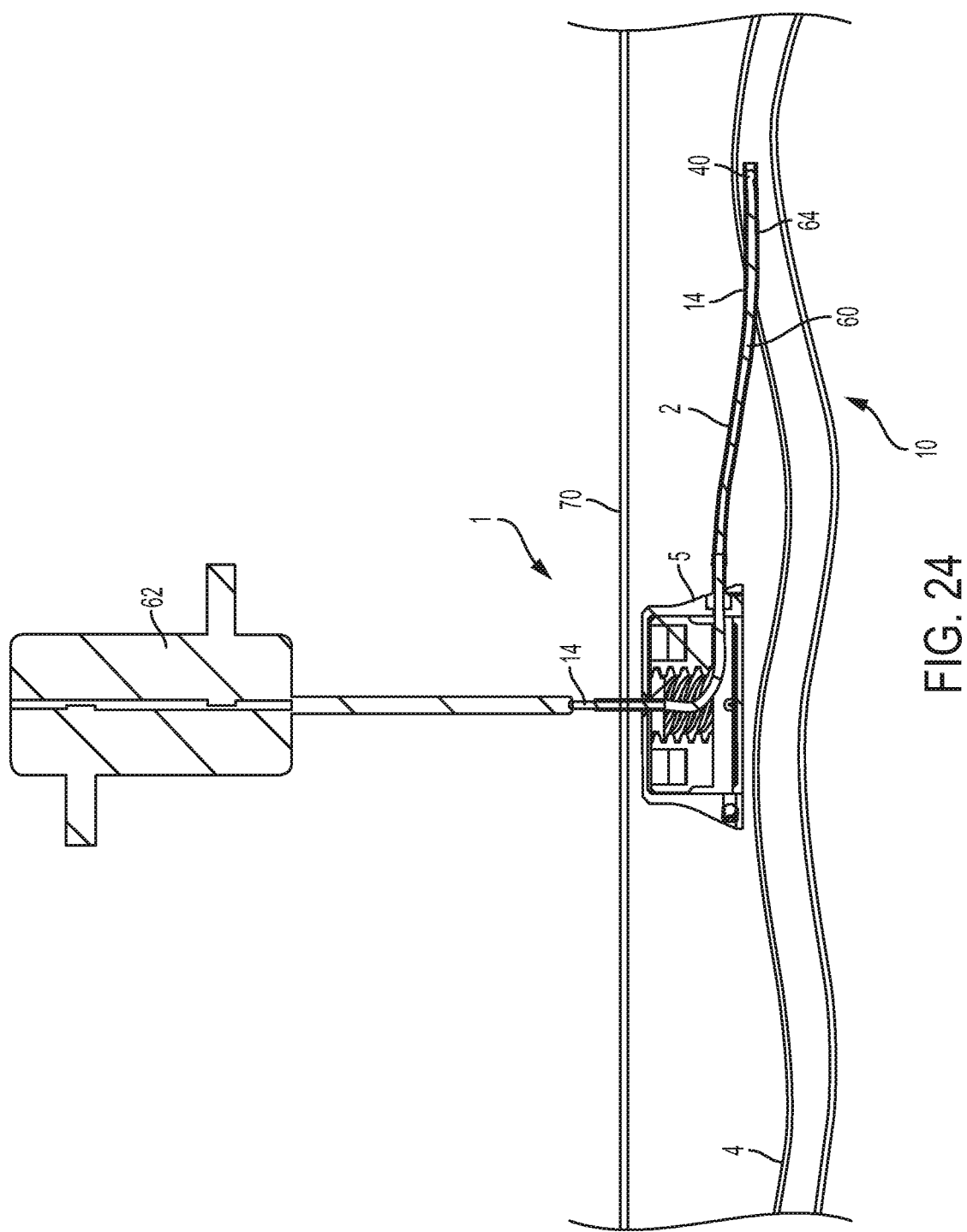
FIG. 24 is a cross-sectional view of an embodiment of a catheter patency system having a light source consistent with the present disclosure.

According to yet another embodiment, the catheter patency system 10, FIG. 24, may include an elongated body 14 inserted within a reflective lumen 60. The elongated body 14, which may comprise a light tube, such as a fiber optic light tube, may be optically coupled to a light source 62 (e.g., but not limited to, an ultraviolet light source) and may include one or more apertures 64 configured to emit light from the light source 62. The light emitted from the light source 62 and the apertures 64 may be configured to sterilize or loosen the adherence of debris 7 within the lumen 8 from within the indwelling catheter system 1. In other embodiments, the reflective lumen 60 may be eliminated and the elongated body 8 may apply light at any location along the length thereof to the debris 7 within the lumen 8 from within the indwelling catheter system 1. The catheter patency system 10 may optionally include any of cleaners 12, flushing lumens/ports, vacuum sources/ports/lumens as described herein, and may also optionally include a balloon 40.

Any of the catheter patency systems 10 described herein may be inserted into an external communication channel (e.g., but not limited to, a needle extending through the host's skin from an access port) and advanced within the indwelling catheter system 1. Alternatively (or in addition), any of the catheter patency systems 10 described herein may be inserted through the host's skin and into the indwelling catheter system 1 (e.g., an access port) using a needle.

Figure 25:
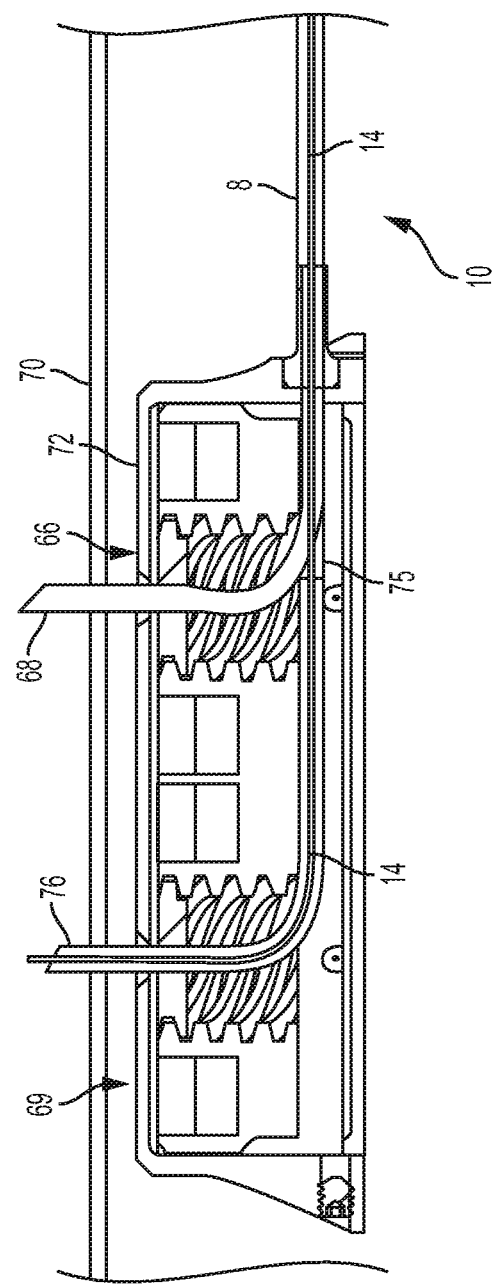
FIG. 25 is a cross-sectional view of an embodiment of an indwelling catheter system including an indwelling catheter patency system consistent with the present disclosure.

Alternatively (or in addition), any of the catheter patency systems 10 described herein may be indwelling within the indwelling catheter system 1 until it is used (and optionally reused, removed, and/or replaced). For example, one embodiment of an indwelling catheter system 1 is generally illustrated in FIG. 25. In particular, the indwelling catheter system 1 may include an access port 66 and a patency port 69. The access port 66 may be configured to provide fluid access to the lumen 8 for delivering and/or withdrawing fluid to/from the lumen 4 of a blood vessel (not shown for clarity). For example, the access port 66 may optionally include a needle 68 configured to be selectively extended and retracted through the user's skin 70. Alternatively (or in addition), the first access port 66 may include a septum 72 through which a separate, external needle (not shown) may pass into a cavity in fluid communication with the lumen 8.

A catheter patency system 10 consistent with the present disclosure may be disposed at least partially within the lumen 8 of the indwelling catheter system 1 and the patency port 69. The patency port 69 may be configured to allow a user (e.g., a surgeon, clinician, host) to gain access to the catheter patency system 10 such that the user can operate the catheter patency system 10 to dislodge debris 7 as described herein. For example, the patency port 69 may be coupled to a portion of the access port 66 and/or the lumen 8 (e.g., by way of a coupler or seal 75) such that the catheter patency system 10 may be disposed therein and the patency port 69 is generally sealed from the access port 66. The patency port 69 may also include a needle 76 configured to selectively extend and retract through the user's skin 70 such that the user can gain access to (e.g., grasp) the catheter patency system 10 and operate the catheter patency system 10 as described herein.

It should be appreciated that any of the features described herein may be combined. For example, any of the cleaners, lumens, balloons or elongated shafts in any of the embodiments described herein may be combined with any of the cleaners, lumens, balloons, elongated shafts in any other embodiments.

While preferred embodiments of the present invention(s) have been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. A medical system, said medical system comprising:
   an indwelling medical device configured to be implanted into a subject including an implantable catheter coupled to an implantable access port,
   a needle having a pointed tip and coupled within said access port, said needle containable within said access port and exposable outside said access port;
   said needle having a lumen with a diameter, said catheter having a lumen with a diameter, and said access port having a lumen in fluid communication with said lumen of said needle and said lumen of said catheter;
   an elongated shaft configured to be received within said lumens of said needle, said access port and said catheter of said indwelling medical device;
   at least one cleaner disposed on said elongated shaft, said at least one cleaner configured to dislodge at least a portion of debris formed within said lumens of said needle, said access port and said catheter of said indwelling medical device;
   said lumen of said access port being a curved lumen defined by said access port which directs said elongated shaft from said lumen of said needle into said lumen of said catheter;
   wherein the lumens of the needle, the access port and the catheter collectively form a lumen of the indwelling medical device having opposing ends;
   wherein a first opening at one of the ends of the lumen of the indwelling medical device is provided by an end of the needle and a second opening at the other end of the lumen of the indwelling medical device is provided by an end of the catheter;
   wherein the lumen of the indwelling medical device, from the first opening to the second opening, is of a cylindrical shape with a corresponding cylindrical surface which defines the lumen;
   wherein, when the access port is implanted in the subject and the needle connected to the access port is exposed outside the access port, the needle is arranged such that the pointed tip is disposed outside the access port and the subject; and
   wherein the needle originates with the implantable access port and, when said indwelling access port is implanted in said subject, selectively extends out of said subject from said indwelling access port as to be exposed outside of said subject and retracts into said subject to said indwelling access port.

2. The medical system of claim 1 wherein:
   said at least one cleaner includes a brush.

3. The medical system of claim 2 wherein:
   said brush includes a plurality of bristles configured to extend generally radially outwardly from said elongated shaft to contact the cylindrical surface of the lumen of the indwelling medical device.

4. The medical system of claim 3 wherein:
   said plurality of bristles are configured to be arranged in an expanded position such that said plurality of bristles contact the cylindrical surface, and a retracted position wherein said plurality of bristles are arranged generally towards said elongated shaft such that an overall cross-section is reduced compared to the expanded position.

5. The medical system of claim 4 further comprising:
   a position selector to urge said plurality of bristles between said expanded and retracted positions.

6. The medical system of claim 1 wherein:
   said at least one cleaner includes an auger.

7. The medical system of claim 1 wherein:
   said at least one cleaner includes at least one protrusion.

8. The medical system of claim 7 wherein:
   said at least one protrusion includes at least a hemispherical configuration.

9. The medical system of claim 7 wherein:
   said at least one protrusion includes a plurality of protrusions separated by flexible segments.

10. The medical system of claim 1 wherein:
    said at least one cleaner includes at least one strand.

11. The medical system of claim 1 wherein:
    said elongated shaft defines at least one flushing lumen having at least one flushing port configured to supply a flushing fluid within said medical device.

12. The medical system of claim 1 wherein:
    said elongated shaft defines at least one vacuum lumen and at least one vacuum port configured to receive dislodged debris from within said medical device.

13. The medical system of claim 1 wherein:
    said cleaner includes at least one fluid aperture configured to provide a fluid to dislodge debris from said indwelling medical device.

14. The medical system of claim 1 further comprising:
    at least one coupler configured to supply a source of fluid to at least one lumen of said elongated shaft.

15. The medical system of claim 1 further comprising:
    at least one balloon positioned at an end of said elongated shaft, said at least one balloon, when inflated, forms a seal with an interior surface of said lumen of said catheter to thereby prevent dislodged debris from exiting said catheter.

16. The medical system of claim 15 wherein:
said elongated shaft defines at least one lumen configured to supply an inflation fluid to said balloon.

17. The medical system of claim 15 wherein:
said elongated shaft defines at least one lumen and wherein said balloon includes an inflation lumen configured to be at least partially disposed within said lumen of said elongated shaft, said inflation lumen configured to supply an inflation fluid to said balloon.

18. The medical system of claim 17 wherein:
at least a portion of said balloon is configured to be moveably disposed within said elongated shaft lumen.

19. The medical system of claim 1 wherein:
the lumen of the indwelling medical device has a constant cross-section from the first opening to the second opening.

20. The medical system of claim 1 wherein:
the pointed tip of the needle faces away from the access port when the needle coupled within the access port is exposed outside the access port.

21. The medical system of claim 1 wherein:
the implantable catheter is an indwelling vascular catheter.

* * * * *